(12) United States Patent
Eicher et al.

(10) Patent No.: US 10,716,906 B2
(45) Date of Patent: Jul. 21, 2020

(54) NEBULIZER AND CONTAINER

(71) Applicant: Boehringer Ingelheim International GmbH, Ingelheim am Rhein (DE)

(72) Inventors: Joachim Eicher, Ingelheim am Rhein (DE); Hubert Hoelz, Oberheimbach (DE); Martin Meisenheimer, Appenheim (DE); Joern-Eric Schulz, Muenster (DE); Herbert Wachtel, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 617 days.

(21) Appl. No.: 15/308,878

(22) PCT Filed: May 4, 2015

(86) PCT No.: PCT/EP2015/059740
§ 371 (c)(1),
(2) Date: Nov. 4, 2016

(87) PCT Pub. No.: WO2015/169759
PCT Pub. Date: Nov. 12, 2015

(65) Prior Publication Data
US 2017/0072148 A1    Mar. 16, 2017

(30) Foreign Application Priority Data
Jul. 5, 2014 (EP) .................................. 14001603

(51) Int. Cl.
*A61M 15/00* (2006.01)
*A61M 11/00* (2006.01)
(Continued)

(52) U.S. Cl.
CPC ........ *A61M 15/0081* (2014.02); *A61M 11/00* (2013.01); *A61M 11/007* (2014.02);
(Continued)

(58) Field of Classification Search
CPC .............. B05B 11/308; B05B 11/0054; A61M 2202/0468; A61M 2202/00007;
(Continued)

(56) References Cited

U.S. PATENT DOCUMENTS 5,833,088 A    11/1998    Kladders
6,283,365 B1 *    9/2001    Bason ................... G06M 1/041
                                                                   235/116
(Continued)

FOREIGN PATENT DOCUMENTS

CA        2863504 A1    7/2013
CN      101141993 A    3/2008
(Continued)

OTHER PUBLICATIONS

International Search Report and Written Opinion for corresponding application PCT/EP2015/059740, dated Oct. 13, 2015.

*Primary Examiner* — Samchuan C Yao
*Assistant Examiner* — Nathan M Le
(74) *Attorney, Agent, or Firm* — Matthew B. Dernier, Esq.

(57) ABSTRACT

A nebulizer and a container with a fluid for such a nebulizer are proposed. The container comprises an indicator device fixedly mounted on the bottom of the container. When a predetermined number of uses of the container (3) with the nebulizer (1) has been reached or exceeded, a signal element becomes visible on the indicator device. The indicator device stops further use of the container in a locked state when a predetermined number of uses has been reached or exceeded. Then, the nebulizer is partially opened and blocked against further use. After replacement of the container including the indicator device, the nebulizer can be used again.

29 Claims, 19 Drawing Sheets

Figure 1:
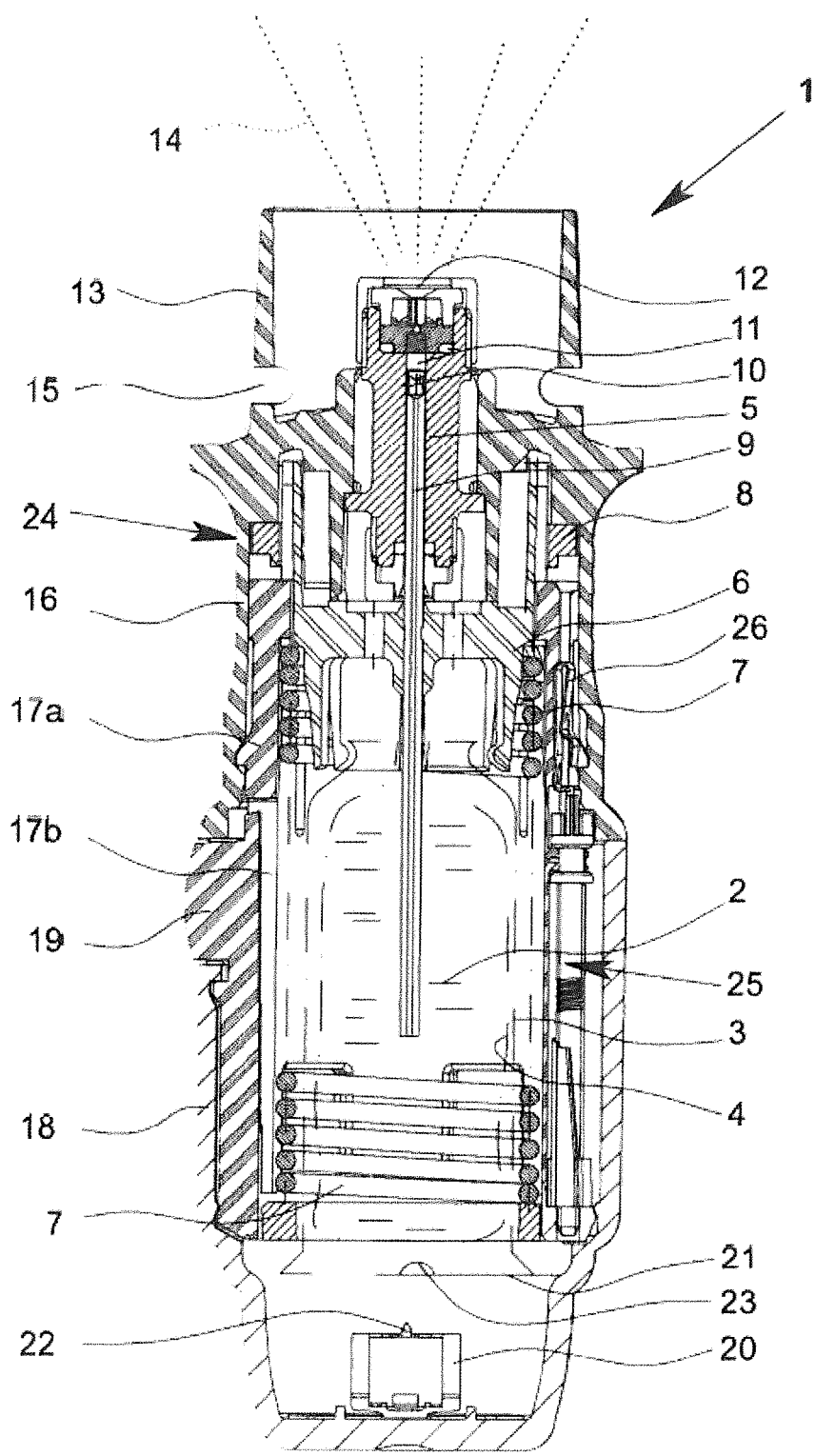

(51) Int. Cl.
*B05B 11/00* (2006.01)
*B65D 83/00* (2006.01)

(52) U.S. Cl.
CPC .... *A61M 15/0021* (2014.02); *A61M 15/0026* (2014.02); *A61M 15/0035* (2014.02); *A61M 15/0036* (2014.02); *A61M 15/0041* (2014.02); *A61M 15/0065* (2013.01); *A61M 15/0071* (2014.02); *A61M 15/0073* (2014.02); *B05B 11/0054* (2013.01); *B05B 11/308* (2013.01); *A61M 2202/0468* (2013.01); *A61M 2205/273* (2013.01); *A61M 2205/583* (2013.01); *A61M 2205/586* (2013.01); *A61M 2207/10* (2013.01); *B65D 83/00* (2013.01)

(58) Field of Classification Search
CPC .......... A61M 15/0021; A61M 15/0065; A61M 11/00; A61M 11/007; A61M 15/0073; A61M 15/0081; A61M 15/0071; A61M 15/0026; A61M 15/0035; A61M 15/0041; A61M 15/0036; A61M 2205/273; A61M 2205/586; A61M 2205/583; A61M 2207/10
See application file for complete search history.

(56) References Cited

U.S. PATENT DOCUMENTS

| | | | |
|---|---|---|---|
| 6,510,847 B1 | 1/2003 | Helgesson | |
| 6,726,124 B2* | 4/2004 | Jaeger | A61M 15/0081 239/333 |
| 7,823,584 B2 | 11/2010 | Geser | |
| 8,474,447 B2 | 7/2013 | Von Schuckmann | |
| 8,656,910 B2 | 2/2014 | Boeck | |
| 9,027,547 B2 | 5/2015 | Hochrainer | |
| 2002/0153005 A1* | 10/2002 | Scarrott | A61M 15/009 128/200.14 |
| 2003/0178020 A1* | 9/2003 | Scarrott | A61M 15/0075 128/200.23 |
| 2004/0211420 A1* | 10/2004 | Minshull | A61M 15/0065 128/203.15 |
| 2005/0087191 A1* | 4/2005 | Morton | A61M 15/0065 128/205.23 |
| 2005/0183718 A1* | 8/2005 | Wuttke | A61M 15/0065 128/200.14 |
| 2005/0209558 A1* | 9/2005 | Marx | A61M 15/009 604/97.03 |
| 2006/0037612 A1* | 2/2006 | Herder | A61M 15/0065 128/203.15 |
| 2007/0062518 A1 | 3/2007 | Geser | |
| 2007/0107720 A1* | 5/2007 | Boeck | B05B 11/0054 128/200.21 |
| 2007/0235027 A1* | 10/2007 | Schuckmann | A61M 15/009 128/200.17 |
| 2008/0017192 A1* | 1/2008 | Southby | A61M 15/009 128/200.23 |
| 2008/0029085 A1 | 2/2008 | Lawrence | |
| 2008/0060643 A1* | 3/2008 | Hodson | A61M 15/009 128/200.23 |
| 2008/0173669 A1 | 7/2008 | Pocock | |
| 2009/0173346 A1* | 7/2009 | Stuart | A61M 15/009 128/203.12 |
| 2009/0293870 A1* | 12/2009 | Brunnberg | A61M 5/31551 128/203.12 |
| 2009/0308385 A1* | 12/2009 | Brewer | A61M 15/0065 128/203.12 |
| 2010/0229857 A1* | 9/2010 | Von Schuckmann | A61M 15/009 128/200.23 |
| 2011/0011393 A1 | 1/2011 | Geser | |
| 2011/0259324 A1 | 10/2011 | Hochrainer | |
| 2011/0290242 A1 | 12/2011 | Bach | |
| 2012/0132199 A1 | 5/2012 | Kiesewetter | |
| 2013/0056888 A1* | 3/2013 | Holakovsky | A61M 15/0065 261/78.2 |
| 2013/0125880 A1* | 5/2013 | Holakovsky | A61M 15/0065 128/200.21 |
| 2013/0125881 A1 | 5/2013 | Holakovsky et al. | |
| 2014/0053838 A1* | 2/2014 | Berenshteyn | A61M 15/0065 128/203.15 |

FOREIGN PATENT DOCUMENTS

| | | |
|---|---|---|
| CN | 102665806 A | 9/2012 |
| EP | 0684047 A2 | 11/1995 |
| EP | 1386630 A1 | 2/2004 |
| EP | 2614848 A1 | 7/2013 |
| GB | 2398253 A1 | 8/2004 |
| JP | 2003504280 A | 2/2003 |
| JP | 2005305370 A | 11/2005 |
| JP | 2009505703 | 2/2009 |
| WO | 9606011 A2 | 2/1996 |
| WO | 2009037085 A1 | 3/2009 |
| WO | 2009115200 A1 | 9/2009 |
| WO | 2010023233 A1 | 3/2010 |
| WO | 2011064160 A1 | 6/2011 |
| WO | 2011064164 A1 | 6/2011 |
| WO | 2012160047 A2 | 11/2012 |
| WO | 2012160052 A1 | 11/2012 |
| WO | 2012162305 A1 | 11/2012 |

* cited by examiner

NEBULIZER AND CONTAINER

The present invention relates to a nebulizer according to the preamble of claim 1, and to a container according to the preamble of claim 28.

WO 2012/162305 A1 discloses a nebulizer. A container can be inserted into a housing of the nebulizer. The housing is closed by a lower housing part. By rotating the housing part the drive spring can be put under tension and fluid can be sucked into a compression chamber of the pressure generator. Simultaneously, the container is moved into the lower housing part in a stroke movement within the nebulizer and when tensioned for the first time the container may be pierced through its base by a piercing element in the lower housing part to allow venting of the container. After manual pressing a button, the drive spring is released and moves the delivery tube into the pressure chamber so that the fluid is put under pressure by the drive spring and is delivered or atomized through a nozzle into a mouthpiece as an aerosol, without the use of propellant gas. Thus, the container is moving axially forth and back during conveying of the fluid to be nebulized, and during pressure generation and nebulization.

The container may be connected inseparably with the housing part by a securing device forming a transportation lock for holding the container unmovable in a delivery state.

The nebulizer comprises an indicator device for counting and/or indicating a number of uses performed or still possible. The indicator device blocks further use in a locked state when a predetermined number of uses has been reached or exceeded with the current container. Then, the container can be replaced together with a housing part and the nebulizer can be used further with the new container.

U.S. Pat. No. 7,823,584 B2 discloses a similar nebulizer, wherein a counter device can be integrated into a housing part that is exchangeable or replaceable together with the container, which is inseparable from the housing part.

WO2009/037085 A1 discloses hand-held device for metered dispensing of sprayable substance (MDI-typ dispenser) with a step-by-step indexing mechanism which moves with a cartridge and which registers dispensing actuations that have been performed with the device. The mechanism comprises oblique slits and associated guide pins, converting a linear movement of the housing of the step-by-step-indexing mechanism into a rotational, step-by-step indexing movement. The central component of the step-by-step indexing mechanism is an epicyclic gear containing a planet wheel, a sunwheel and a gear rim.

WO 2010/023233 A1 discloses another atomizer of the type of an MDI with a counting device which comprises a guide element which converts an axial movement to a partial rotational movement for driving a counter ring. The conversion is achieved by way of a guide track and an inclined plane associated to the guide element.

Object of the present invention is to provide a nebulizer and a container for a nebulizer allowing easy and/or secure operation and handling and/or a compact and/or reliable construction, preferably while allowing replacement of the container without replacement of any housing part of the nebulizer.

The above object is achieved by a nebulizer according to claim 1 or by a container according to claim 19 or 28. Preferred embodiments are subject of the subclaims.

The present invention relates to a nebulizer for nebulizing a fluid, preferably liquid medicament, from a preferably replaceable container containing the fluid, and relates to the container. An indicator device is provided for counting and/or indicating the number of uses already performed or still possible with the container.

In particular, the indicator device or an associated locking device can lock the container and/or nebulizer or can cause the locking of the container and/or nebulizer against further use in a locked state when a predetermined number of uses has been reached or exceeded with the respective container.

In particular preferably, the indicator device enters a locked state when a predetermined number of uses has been reached or exceeded with the respective container and the nebulizer comprises a locking device which causes the locking of the nebulizer against further use with a container in the locked state.

Preferably, the nebulizer comprises a housing part which can be detached from the nebulizer or opened for replacing the container.

According to one aspect of the present invention, the indicator device is preferably adapted to at least partially open or to cause at least partial opening of the nebulizer and/or housing part in the locked state and/or when the locked state is reached and/or the indicator device is adapted to prevent the complete closure of the nebulizer and/or housing part in the locked state. In particular, this allows a very compact and simple construction and/or secure operation. In particular, this supports an intuitive handling.

According to a further aspect of the present invention, the indicator device in the locked state blocks complete assembly of the container with the nebulizer or with the nebulizer housing and/or housing part in the locked state of the nebulizer. In particular, this allows a very compact and simple construction and/or secure operation. In particular, this supports an intuitive handling.

Preferably, this prevents re-use or re-insertion of an already used container and, thus, allows a very simple and secure construction.

According to a further aspect of the present invention, the indicator device is preferably adapted to block full axial or stroke-like movability of the container within in the nebulizer in the locked state. This allows very compact and simple construction. Preferably, the number of necessary parts and components can be minimized. Further, this allows secure operation.

Preferably the nebulizer and/or container cannot be used anymore in the locked state when the indicator device has detected that a predetermined number of uses has been reached or exceeded, in particular with the respective container.

According to another or further aspect of the present invention, the indicator device may either directly or indirectly lock or initiate or trigger locking of the nebulizer and/or container against further use. In particular, the indicator device causes the actuation of a locking device of the nebulizer. Preferably, an indirect actuation is realized by means or via at least partial opening of the nebulizer or its housing or housing part in order to lock the nebulizer against further use with the current container.

Preferably, the indicator device comprises a blocking part which blocks further use of the container and/or nebulizer in the locked state.

Preferably, the blocking part causes the actuation of a locking device in the nebulizer in the locked state. This actuation can be realized indirectly, in particular by opening the nebulizer which results in an actuation of the locking device or its locking element. Thus, further use, in particular further dispensing or nebulization of fluid can be prevented or blocked in the locked state.

Preferably, the nebulizer is blocked (automatically) against further use or tensioning if the nebulizer housing or housing part is at least partially open or opened or if, with other words, when the nebulizer or its housing is not (completely) closed.

It is also possible that the nebulizer is not immediately blocked against further use when the indicator device enters the locked state. Instead, the indicator device may initiate or cause or trigger in its locked state that the locking device is going to block the nebulizer against further use, e.g. during the next actuation or tensioning or the like. Thus, the locking device may enter its locking state later, e.g. after at least partial opening of the nebulizer and/or at least partial tensioning of the nebulizer or rotation of the housing part or inner part of the nebulizer or the like.

Therefore, the blocking of the nebulizer can be initiated or caused by the indicator device not only indirectly, but alternatively or additionally also later during further handling, operation, actuation or the like. In the latter case, the indicator device blocks or initiates or causes blocking of the nebulizer and/or container against further use also preferably in the sense of the present invention.

Preferably, the locking of the nebulizer against further use can be overcome by replacing the container, in particular including the indicator device, against one not yet used.

According to another aspect of the present invention, the indicator device is preferably inseparably connected with the container or with a container housing of the container, but separable from the nebulizer or its housing and from the housing part, so that the indicator device is replaceable together with the container. This allows reuse of the nebulizer and the housing part with another container including another indicator device. Thus the overall size of the components to be exchanged is kept small, so that the replacement packages are size reduced, so that transport of a large number of packages is facilitated.

Preferably, the indicator device is fixedly arranged at a bottom of the container and/or opposite to an outlet of the container. This allows a very compact construction. Further, the indicator device does not interfere with the fluidic connection of the container to the nebulizer or vice versa.

According to a further aspect of the present invention, the indicator device comprises preferably a piercing element for opening and an aeration opening. In particular, this allows a very compact construction and/or supports secure operation.

Preferably, the indicator device comprises an indicator element and an actuation element for (directly or indirectly) indexing the indicator element or for actuation a transmission and/or a step-by-step mechanism indexing the indicator element. Preferably, the step-by-step indexing mechanism comprises a reduced transmission. In particular, the indicator element displays an indication of the number of uses already performed or still possible with the respective container.

Preferably, a linear movement of the actuation element causes a rotational movement of the indicator element.

Even more preferably, the actuation element is set in motion by a relative longitudinal movement between the container with the indicator device and the housing and/or housing part of the nebulizer.

Figure 2:
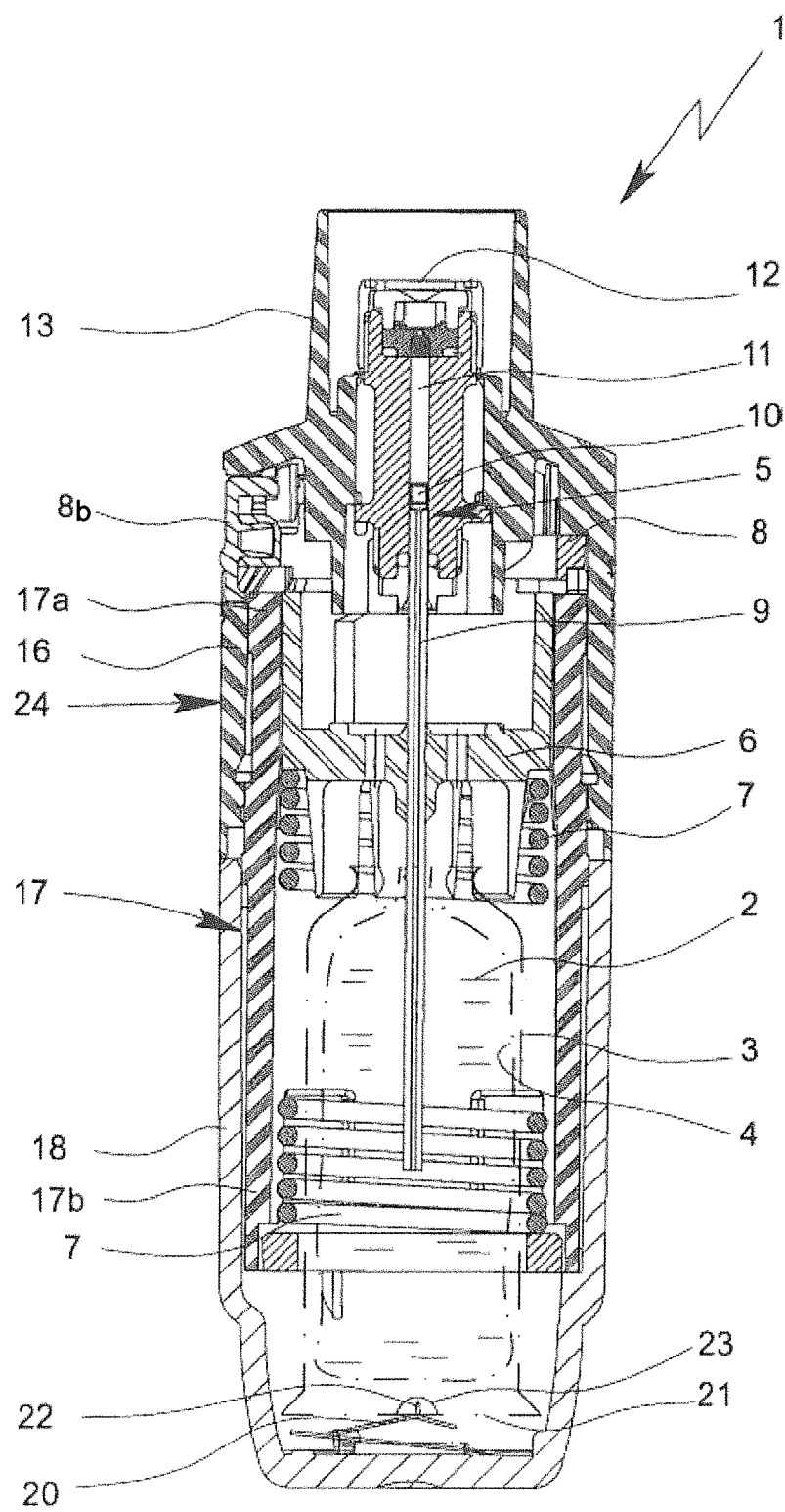
Figure 3:
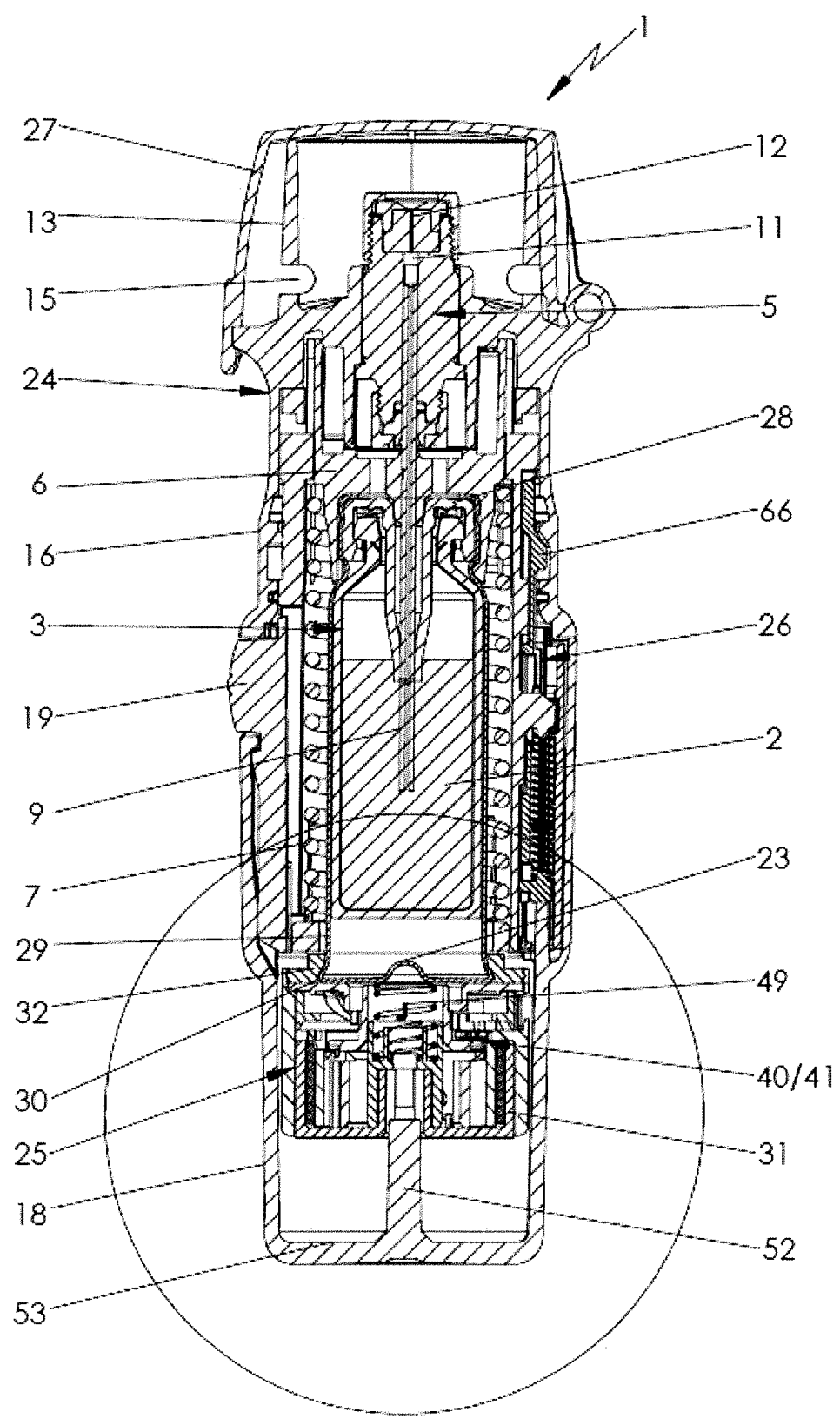
Figure 4:
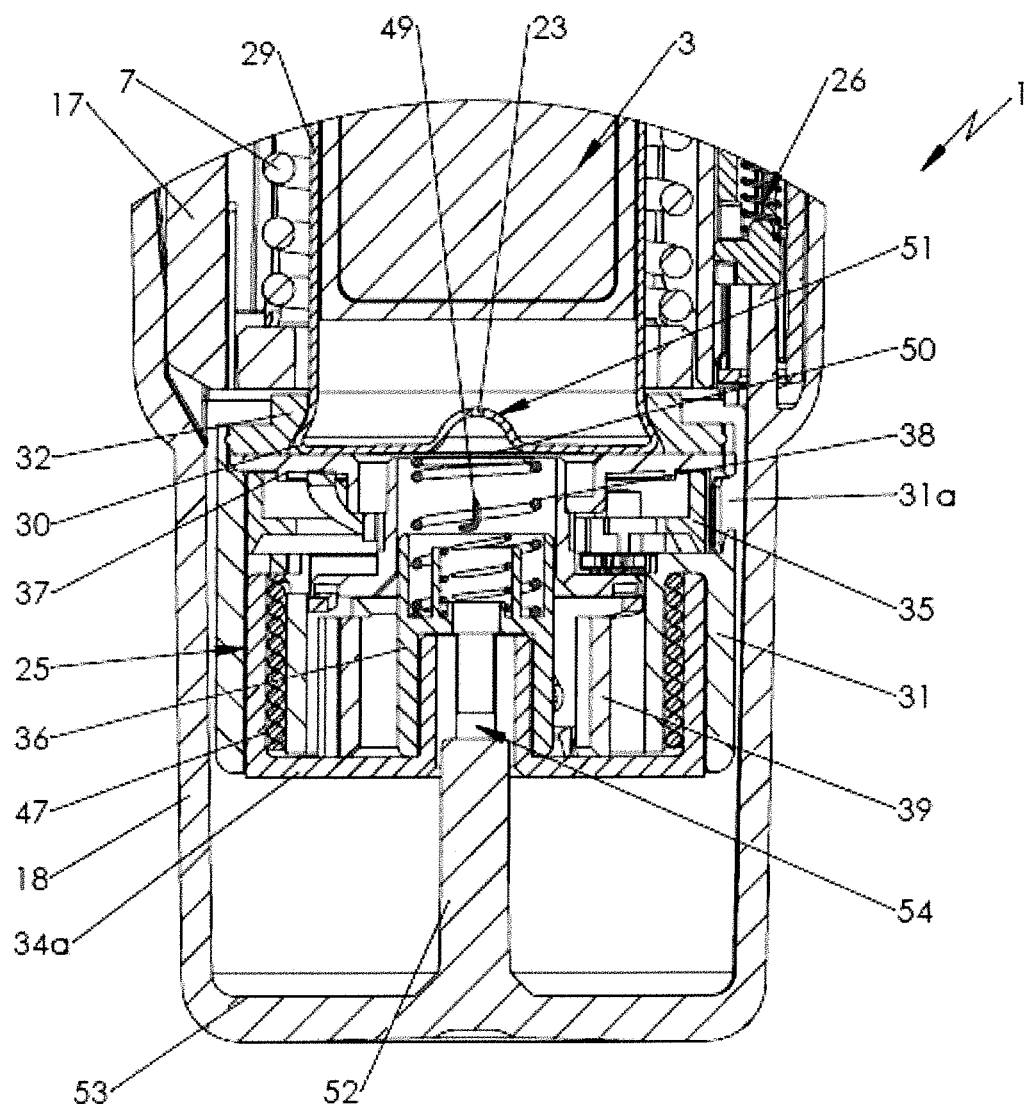
Figure 5A:
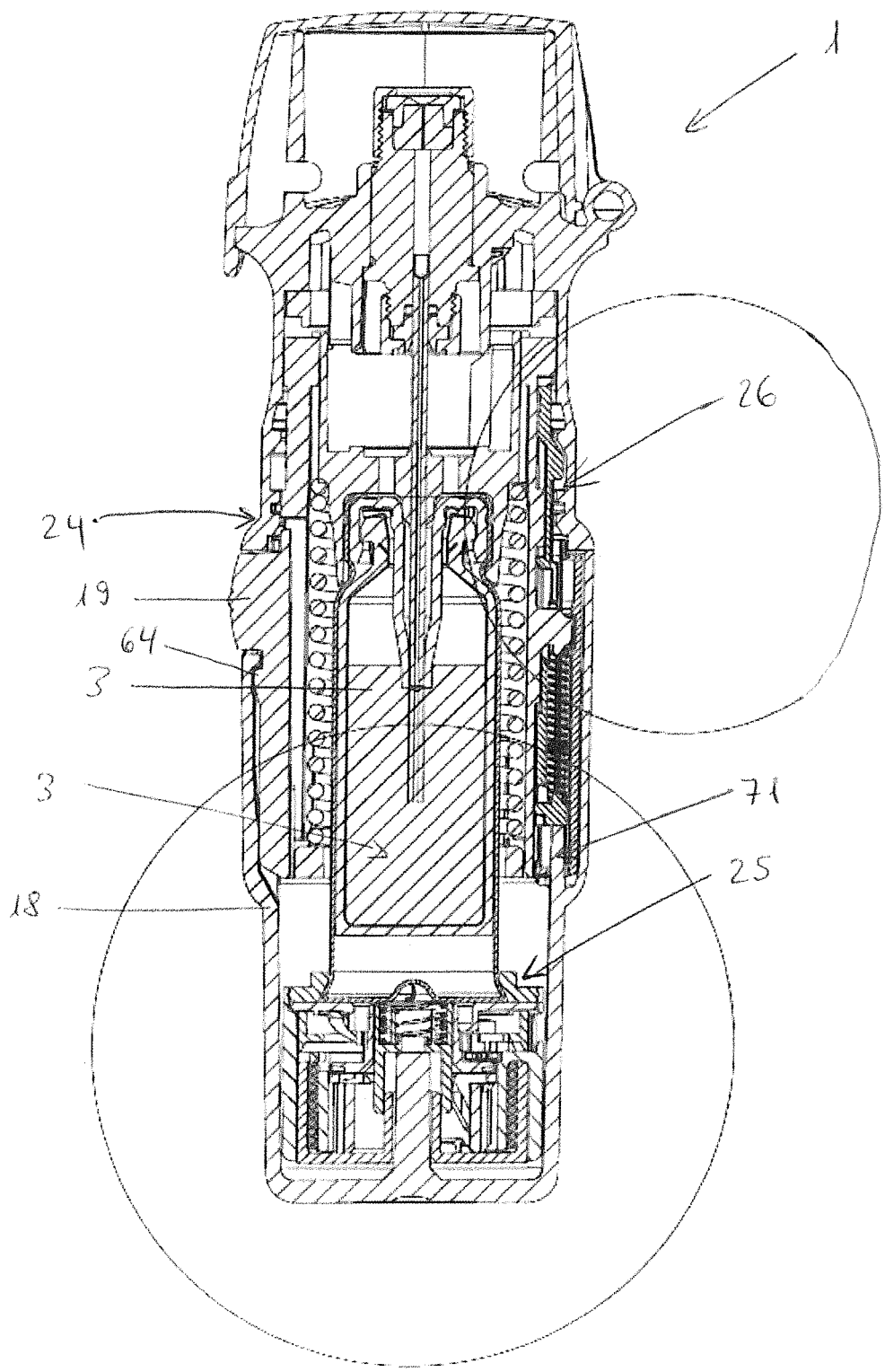
Figure 5B:
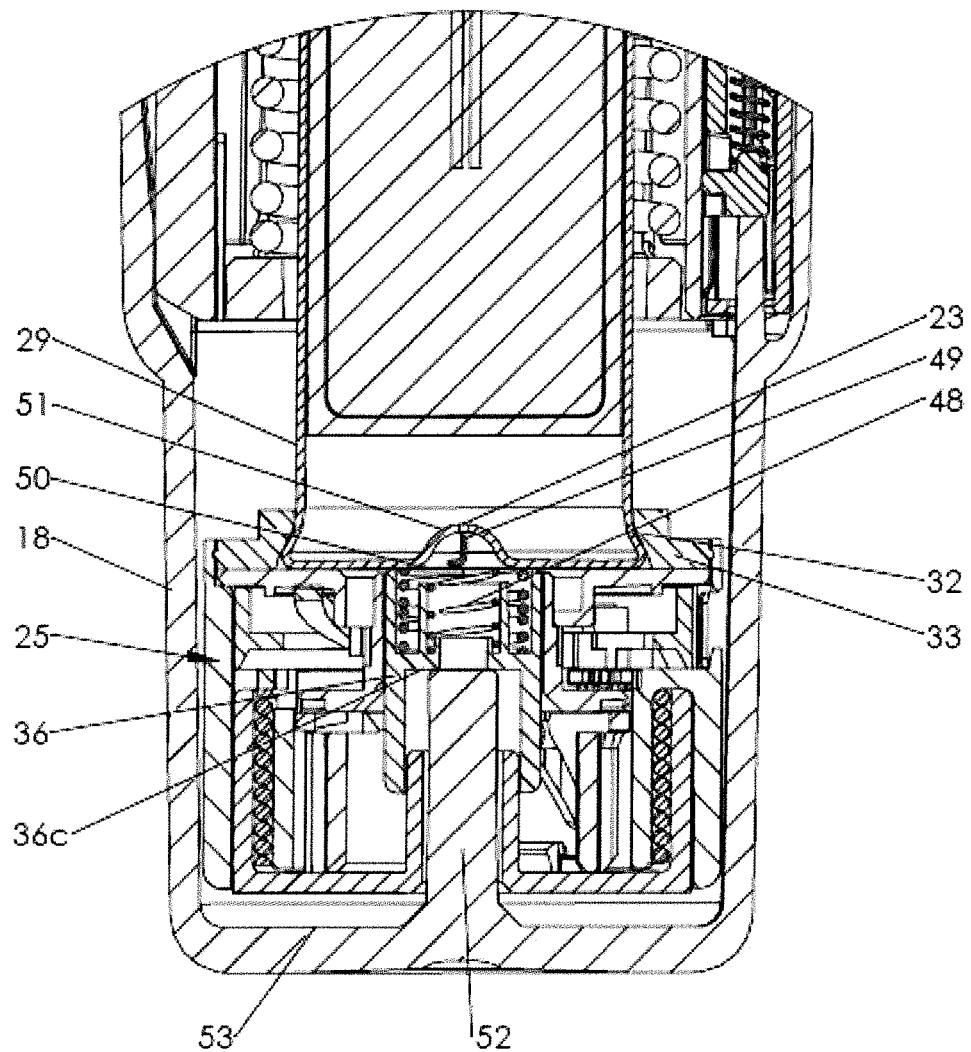
Figure 5C:
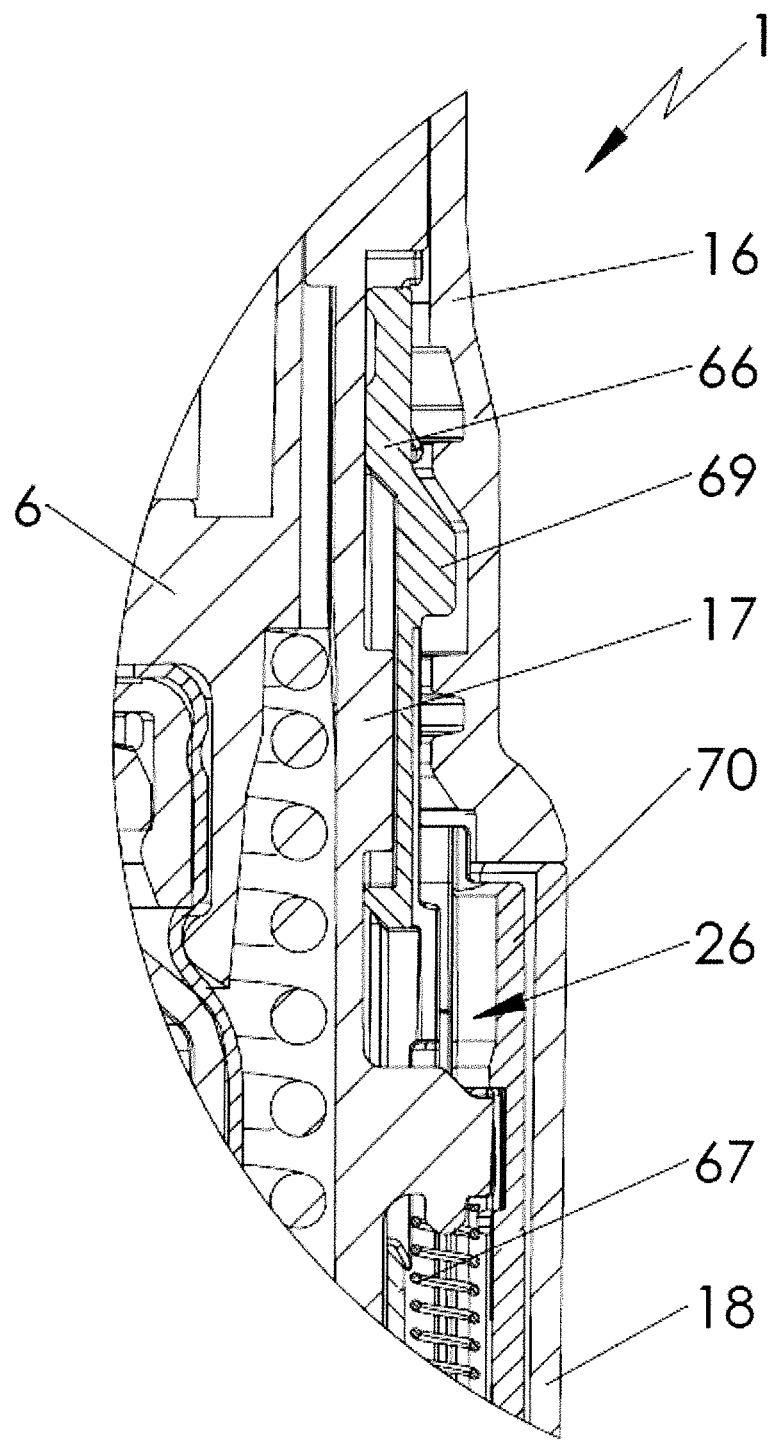

Preferably, the indicator device comprises a signal element or flag which becomes visible or more visible to the user of the nebulizer when the locked state of the indicator device is entered and/or when the predetermined number of uses of the nebulizer with the container associated to this indicator device in its locked state has been reached or exceeded and/or that the container is empty.

Preferably, the signal element is moved from a (initial) first position in the housing of the indicator device to a second position in which it partly extends from the indicator housing and/or where it is more visible than in the first position.

Preferably, an indicator element in the indicator device causes the movement of the signal element from the first into the second position.

Preferably, the signal element or a part of it (a part that is visible in the second position) has a color which enhances the visibility of the signal element in the locked state of the indicator device (red, for instance). In particular, this allows an enhanced user guidance and/or enables to user to identify the locked state of the indicator device and the associated container before the next use of the nebulizer is due.

Preferably the indicator device (25) comprises a blocking spring (43) (or another constructional feature) preventing a back movement of the signal element (34) or flag from the second position to the first position.

According to another aspect of the present invention, preferably, the blocking part forms or is formed by or is made integral with or is identical with the signal element. In particular, this allows a very compact and simple construction and/or secure operation. Preferably, the number of necessary parts and components can be minimized.

According to another aspect of the present invention, the blocking part is preferably integrated into a housing of the indicator device. In particular, this allows a very compact and simple construction and/or secure operation. Preferably, the number of necessary parts and components can be minimized.

According to a further aspect of the present invention, the blocking part is preferably moveable in parallel to a longitudinal or dispensing direction of the container or nebulizer. In particular, this allows for a good visibility of the locked state and/or for secure operation. Preferably, the number of necessary parts and components can be minimized.

According to a further aspect of the present invention, in the locked state the blocking part preferably disables the counting and/or the actuation of the counting mechanism in the indicator device and/or an interaction of the driving part with the indicator device in the locked state.

Preferably, in the locked state the blocking part prevents interaction of a driving part (attached to the housing or the housing part of the nebulizer) with the counting mechanism of the indicator device, for instance by preventing interaction of the driving part with the actuation element and/or by disengaging an advancing element in the indicator device and/or by closing or disabling an insertion opening (of the indicator housing). In particular, in the unlocked state, the insertion opening is for receiving a driving part attached to the housing or the housing part of the nebulizer, so that upon a relative movement between the indicator housing and/or the container and the nebulizer housing, the driving part actuates the indicator device in particular such that a use of the nebulizer is counted and/or indicated in the indicator device. In particular, this allows a very compact and simple construction and/or secure operation. Preferably, the number of necessary parts and components can be minimized.

The above aspects of the present invention and the further aspects described below can be realized independently from each other, and in any combination.

Further advantages, features, characteristics and aspects of the present invention will become apparent from the claims and the following description of a preferred embodiment with reference to the drawings. It shows:

FIG. 1a schematic section of a known nebulizer in a non-tensioned state;

FIG. 2 a schematic section, rotated 90° compared with FIG. 1, of the known nebulizer in a tensioned state;

FIG. 3 a schematic section of a nebulizer with an inserted container in a non-tensioned state according to a preferred embodiment of the present invention;

FIG. 4 a partial enlargement of the encircled part of FIG. 3;

FIG. 5a a schematic section of the nebulizer with an inserted container (similar to FIG. 3) in a tensioned state according to a preferred embodiment of the present invention;

FIG. 5b a partial enlargement of the bigger encircled part of FIG. 5a; the section is similar to of FIG. 4, but showing the tensioned state of the nebulizer;

FIG. 5c a partial enlargement of the smaller encircled part of FIG. 5a (the nebulizer is in the unlocked state).

Figure 6:
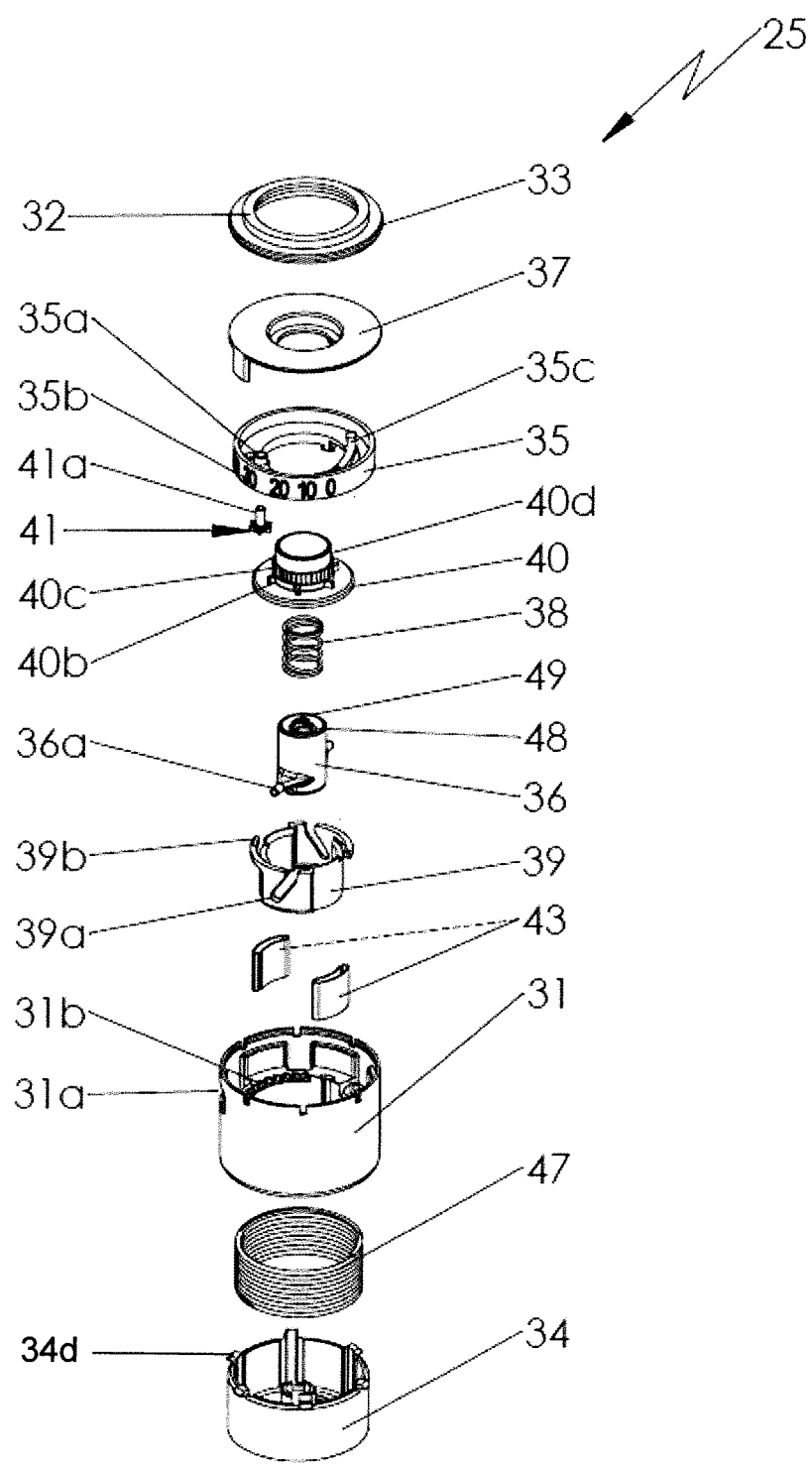
Figure 7:
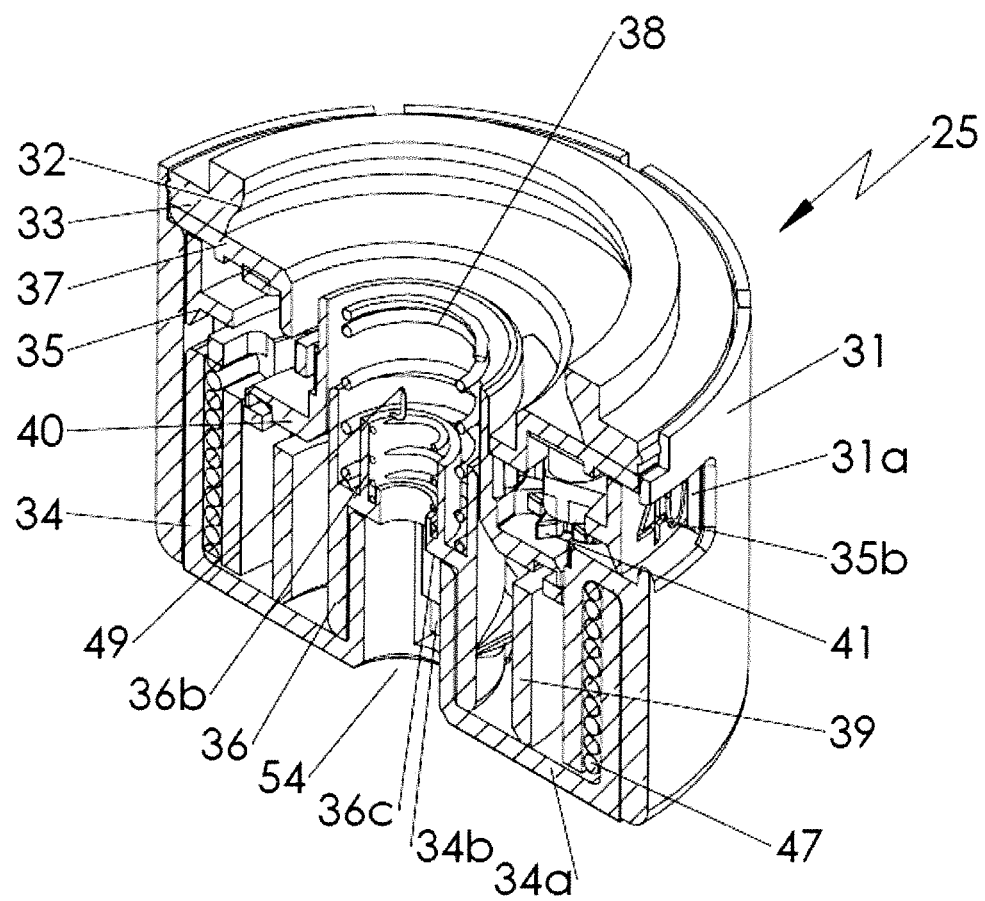
Figure 8:
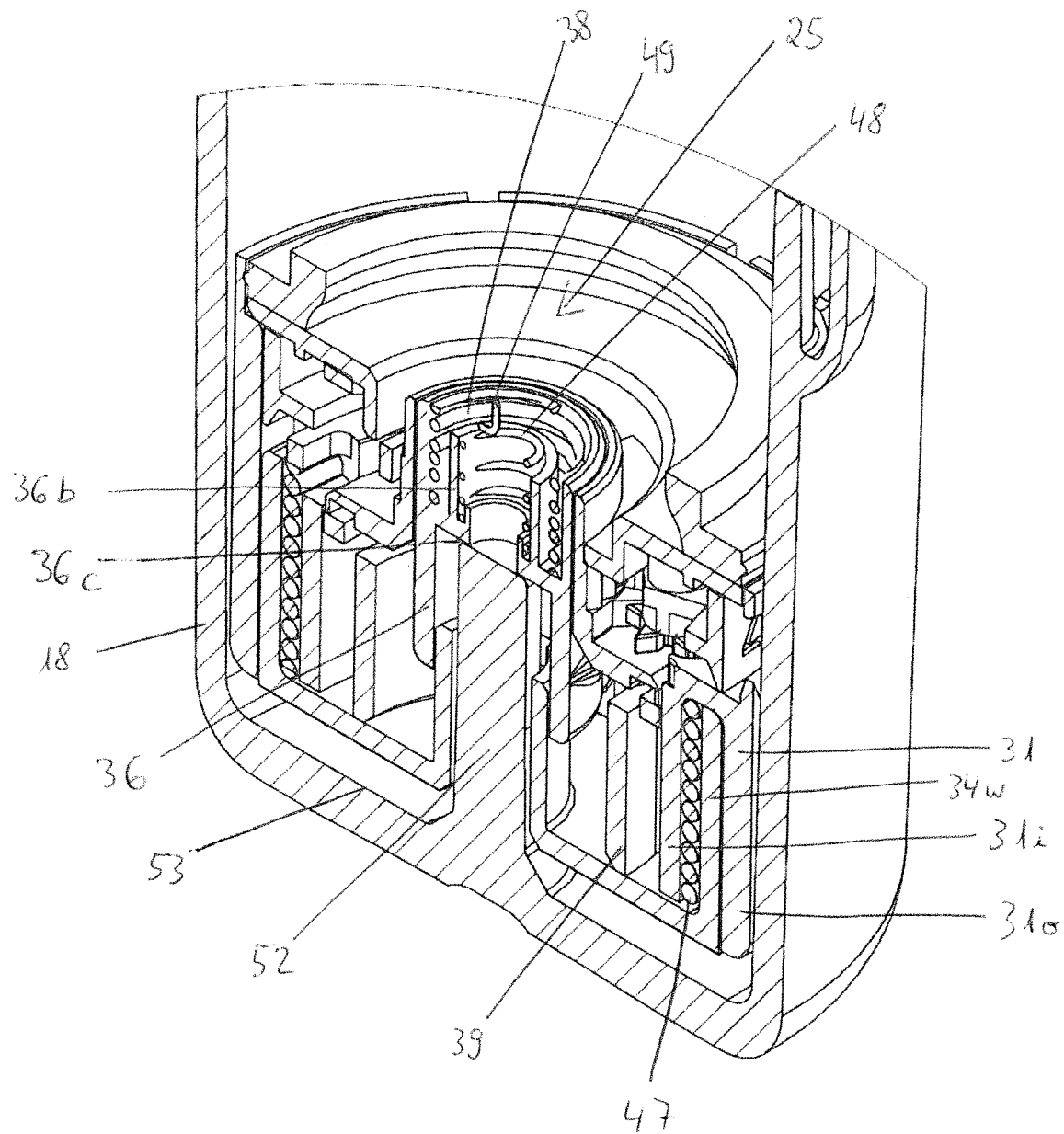
Figure 9:
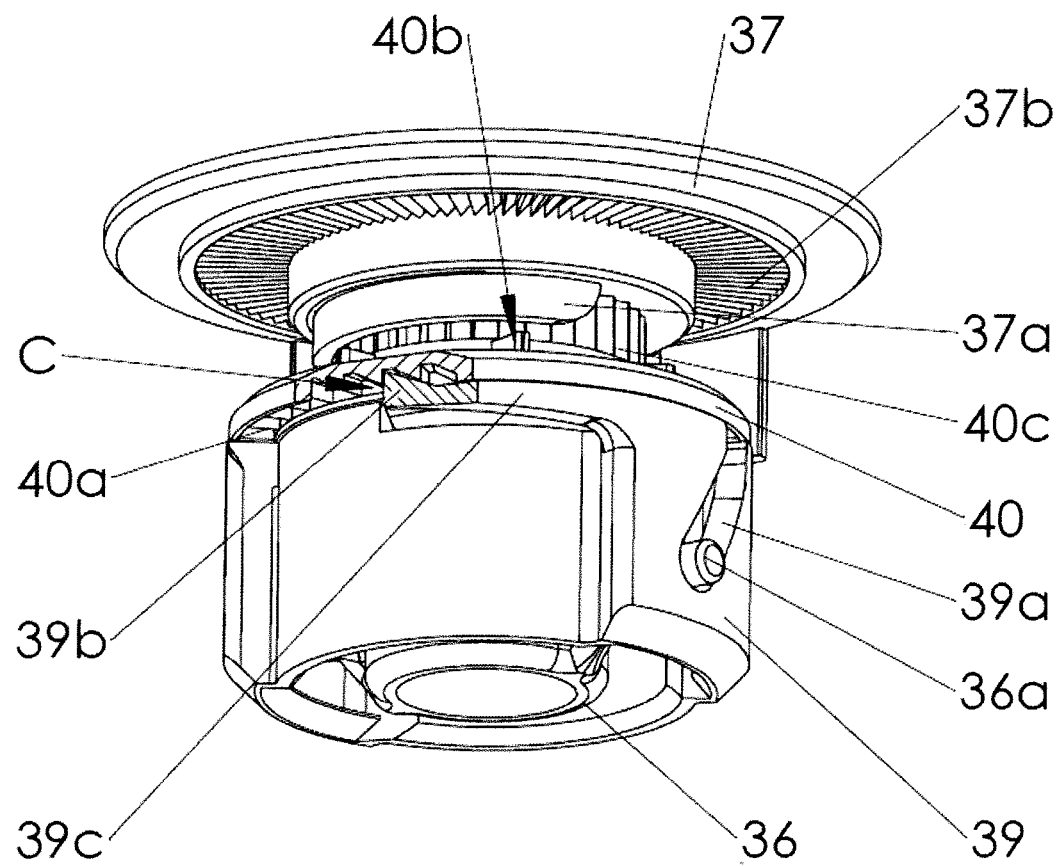
Figure 10A:
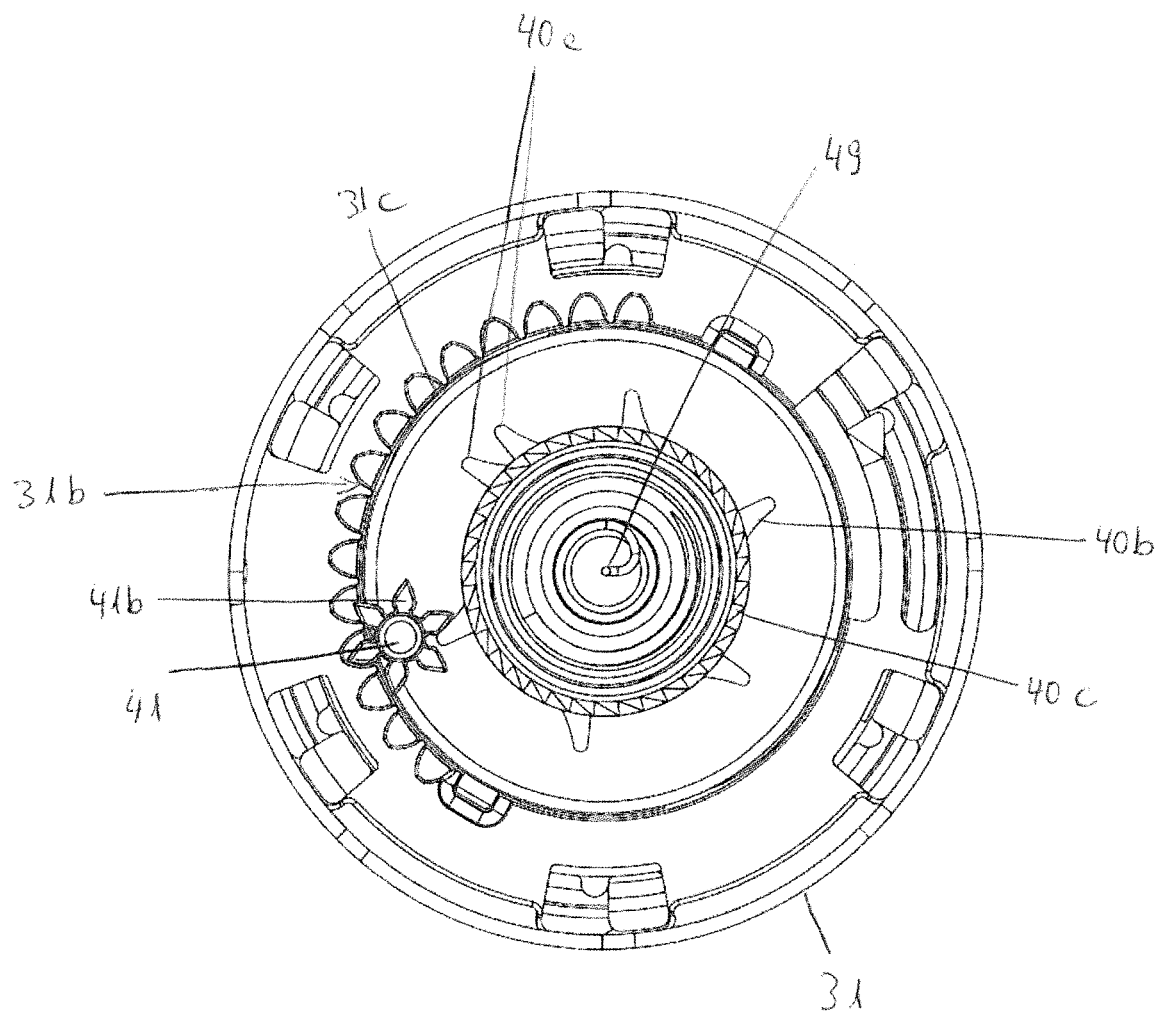
Figure 10B:
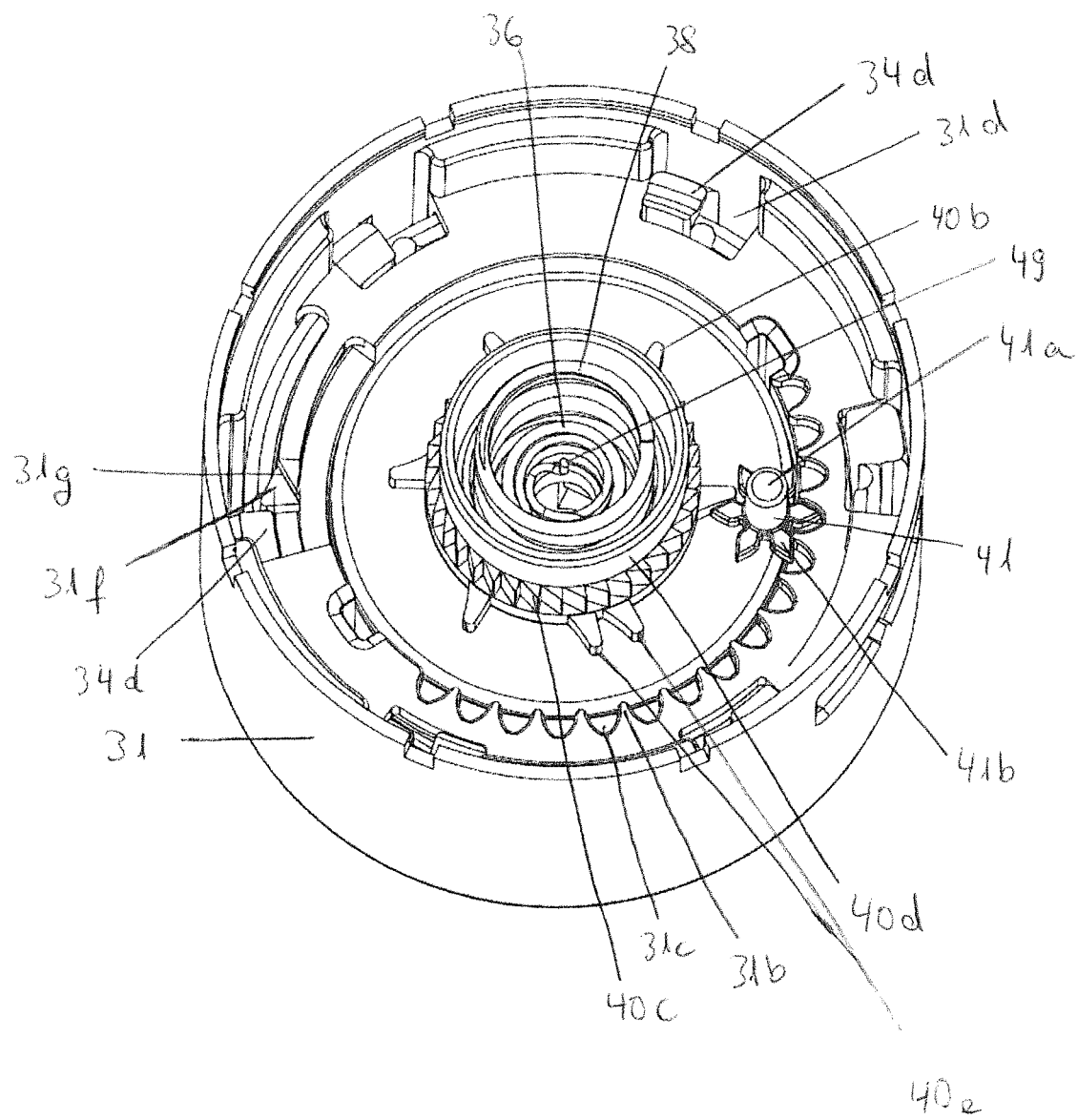
Figure 10C:
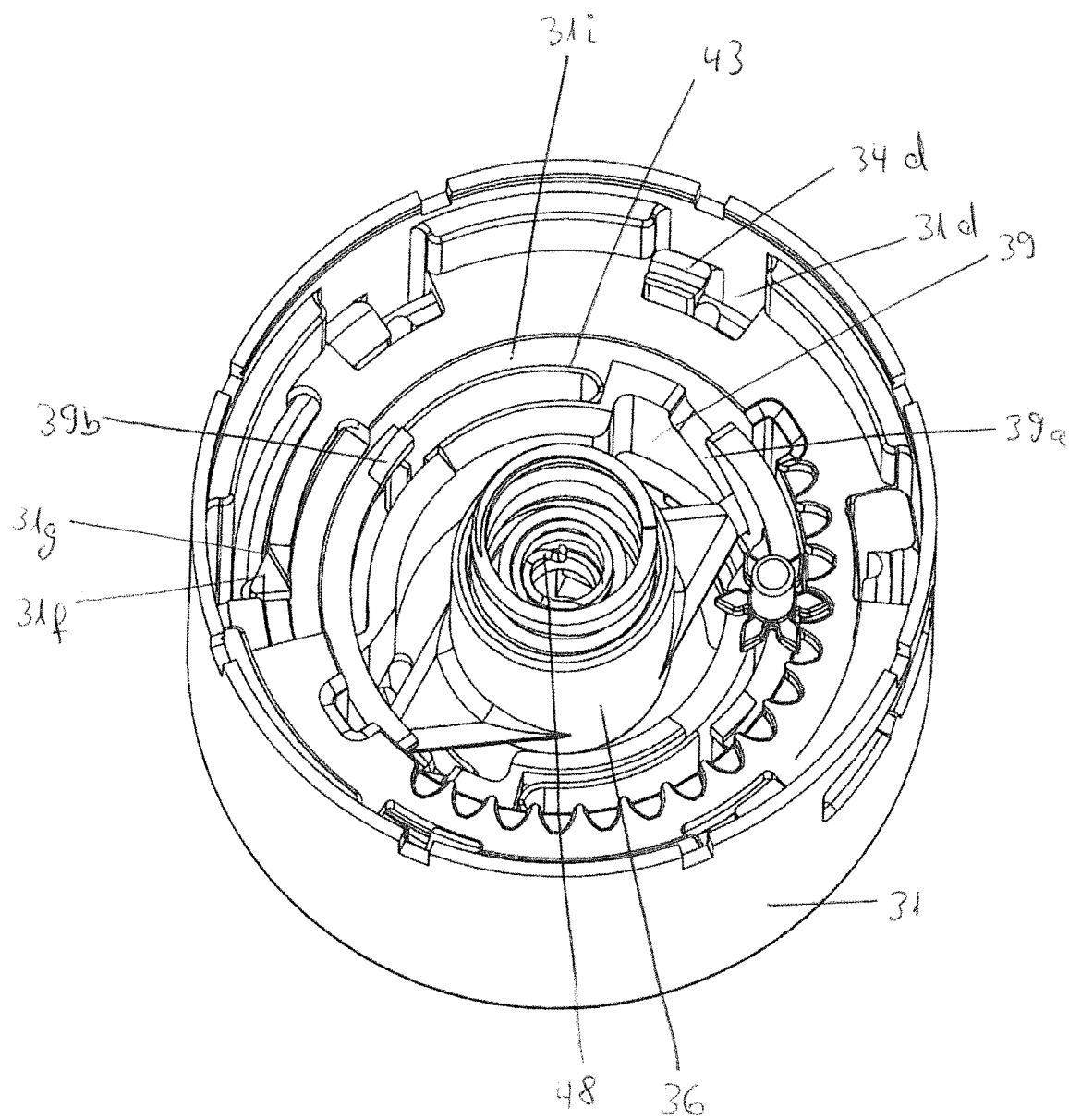
Figure 11:
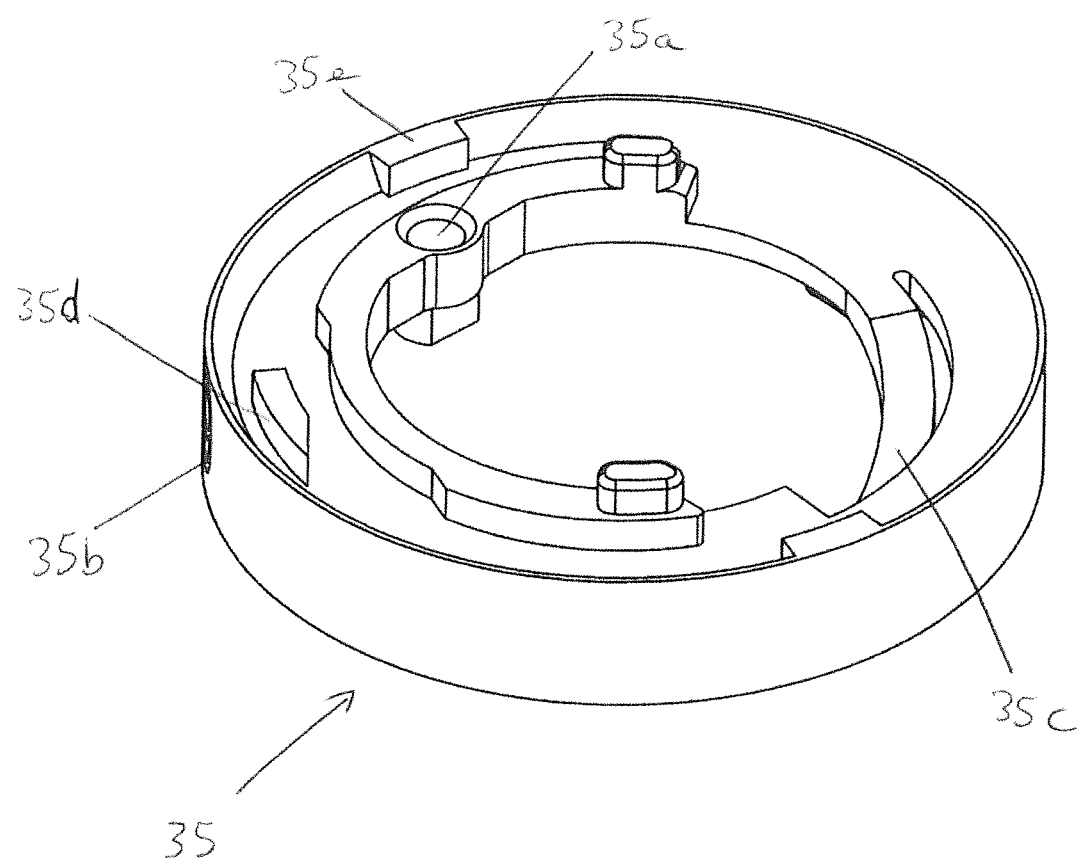
Figure 12:
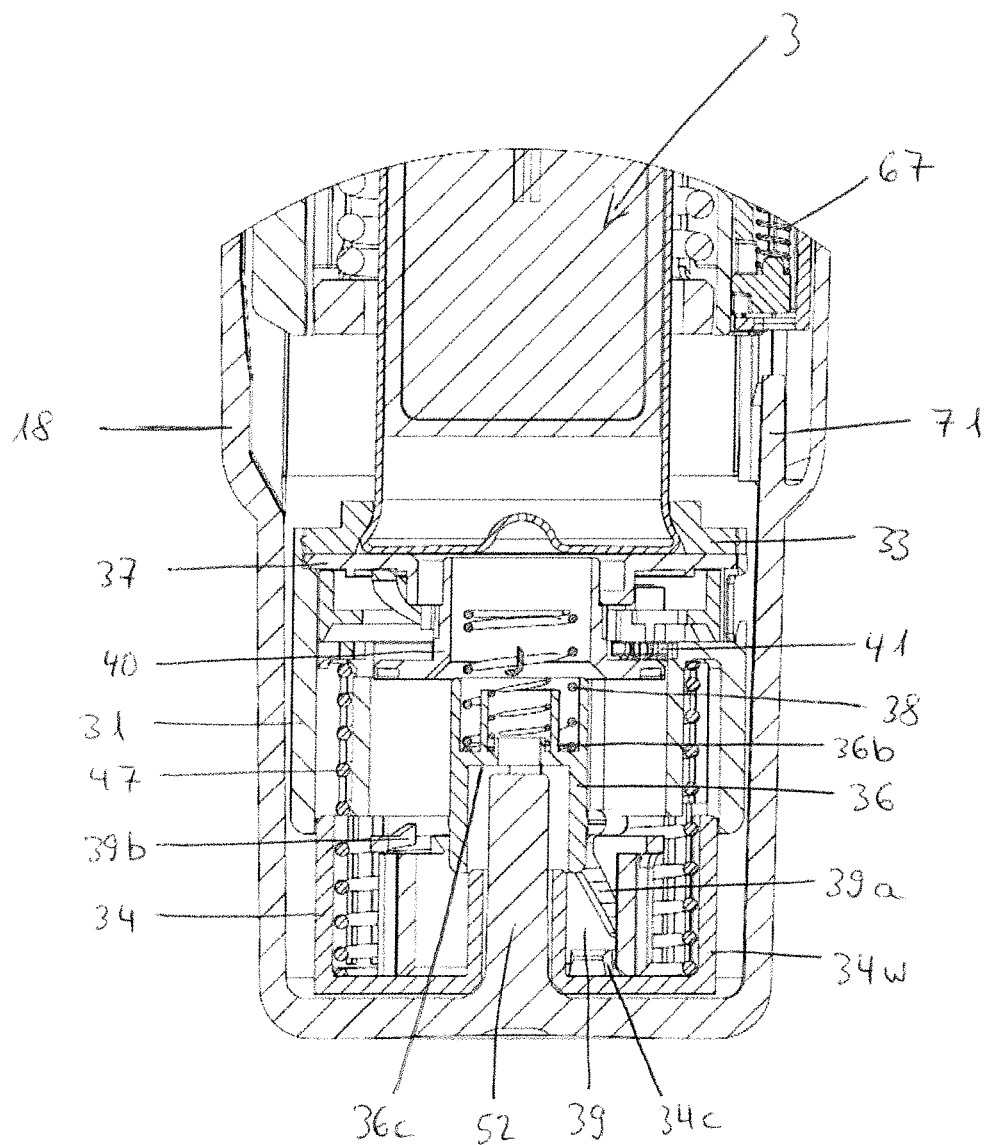
Figure 13:
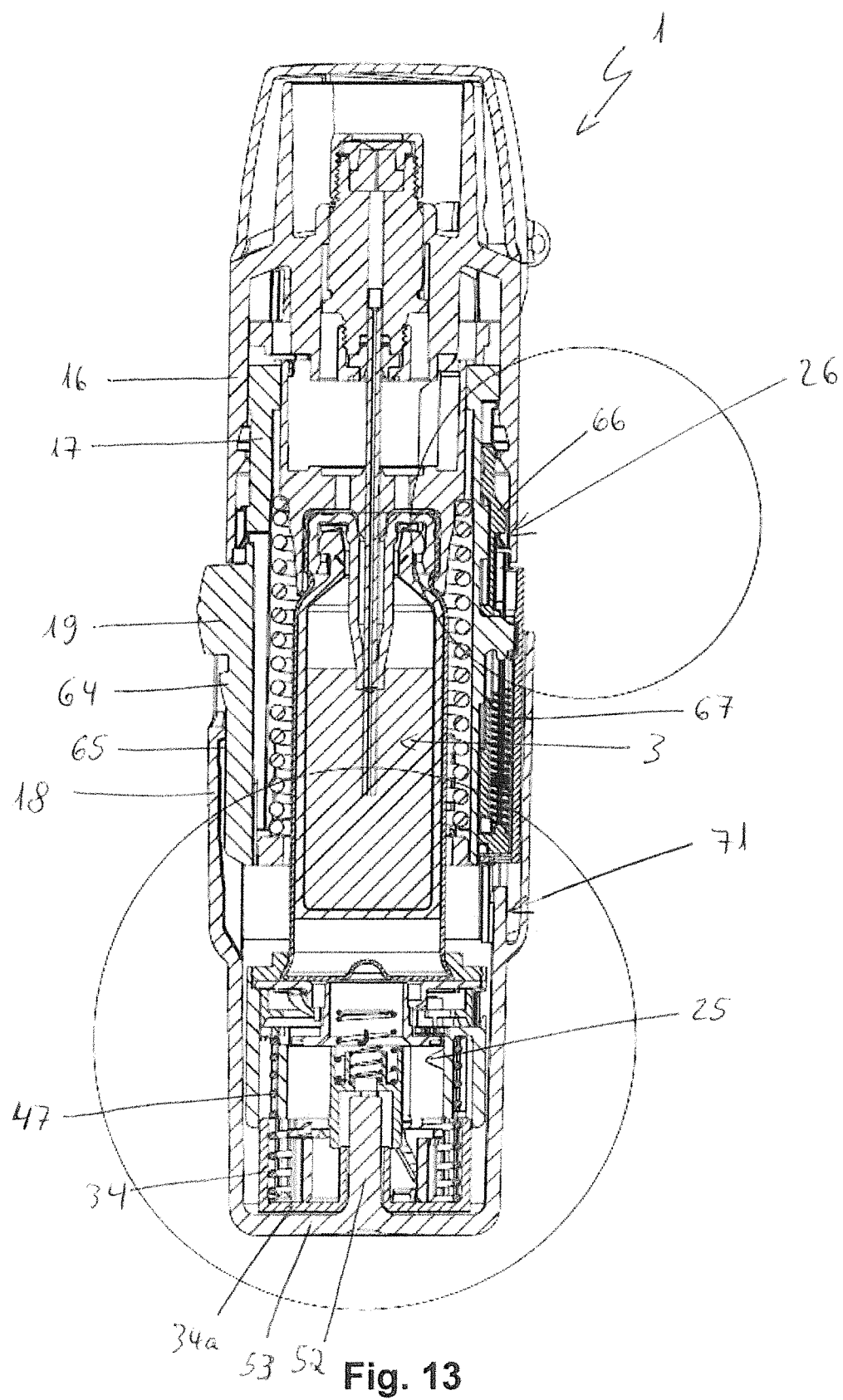
Figure 14:
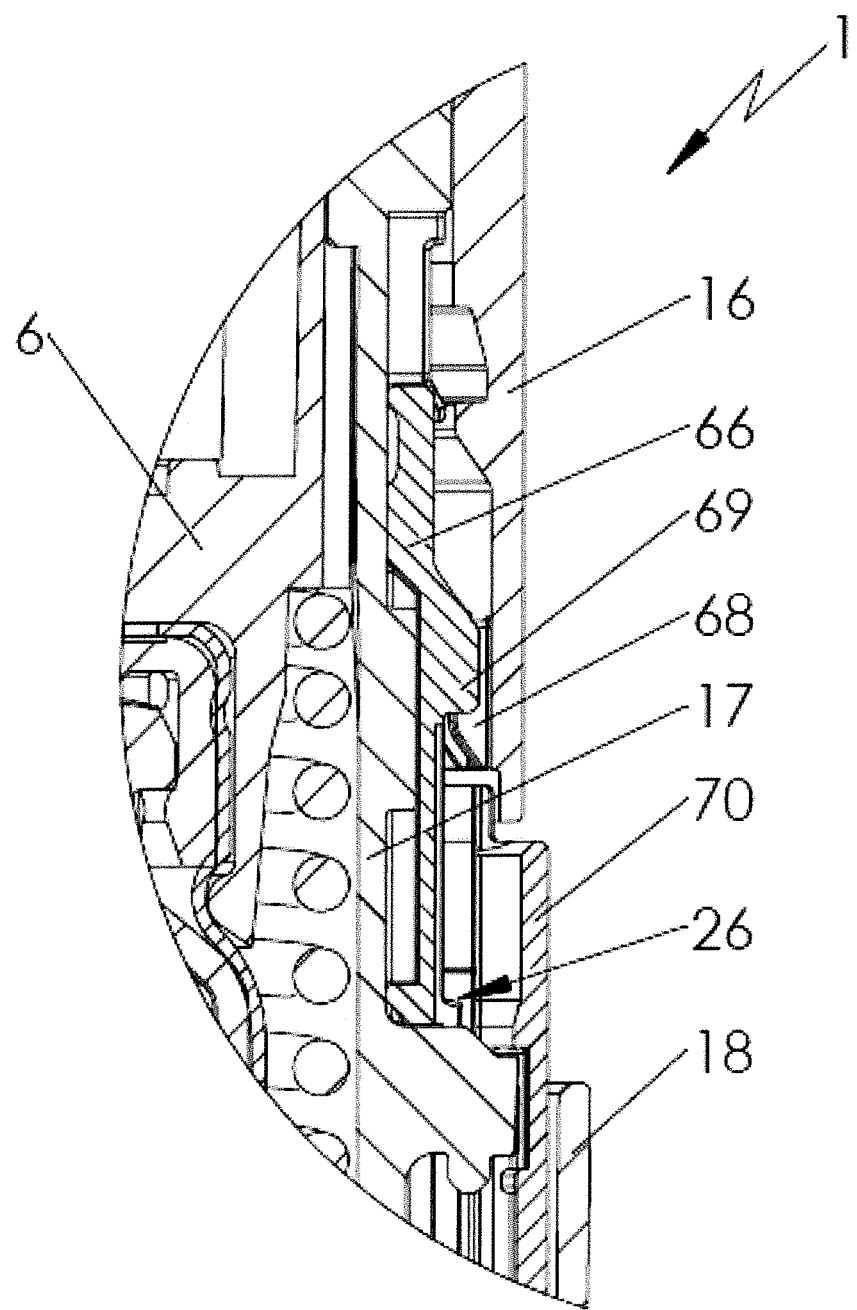
Figure 15:
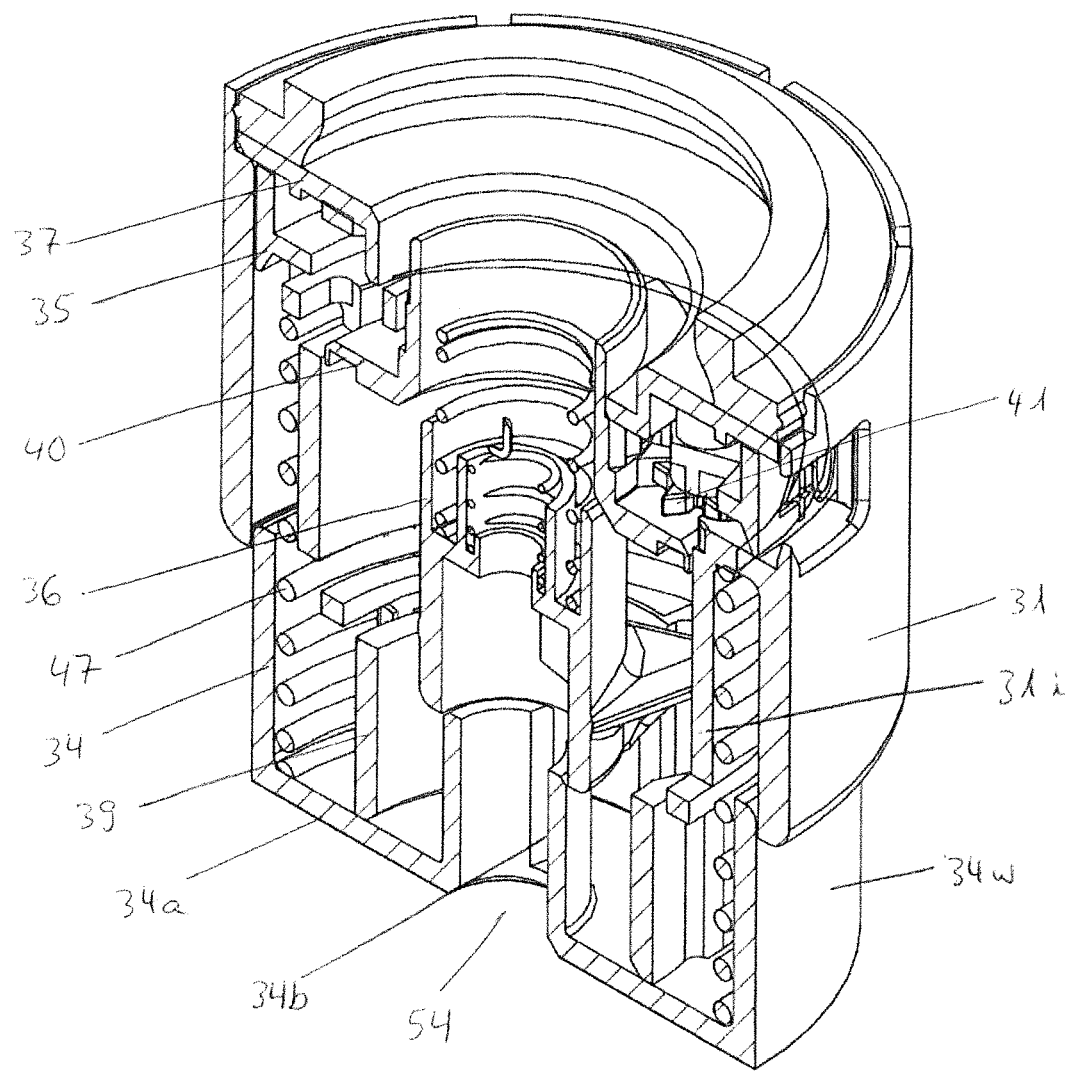

FIG. 6 a schematic exploded view of an indicator device according to a preferred embodiment of the present invention;

FIG. 7 a perspective section of the indicator device in an initial state (container and nebulizer parts are omitted);

FIG. 8 a perspective section of the indicator device in an actuated state (container is omitted, interaction with housing part 18 of the nebulizer is shown);

FIG. 9 a perspective, partly sectional view on an assembly of selected interacting parts of the indicator device;

FIG. 10a another assembly of selected interacting parts of the indicator device (viewed from the cartridge side of the indicator device);

FIG. 10b perspective view on the same assembly of selected interacting parts of the indicator device as in FIG. 10a;

FIG. 10c same as FIG. 10b but with omission of one of the parts (omission of transmission 40);

FIG. 11a perspective view of an indicator element of the indicator device;

FIG. 12 a partial section of the nebulizer similar to FIG. 4, but with an indicator device of the container in a locked state (the nebulizer is in a tensioned state);

FIG. 13 a schematic section of the nebulizer in the locked state after next tensioning with partially opened housing part and with locked locking device (FIG. 12 corresponds to a bigger encircled part of FIG. 13);

FIG. 14 a partial enlargement of the smaller encircled part of FIG. 13 (section similar to FIG. 5c, but with the nebulizer in the locked state);

FIG. 15 a perspective section of the indicator device in a locked state;

In the Figures, the same reference numerals are used for identical or similar parts, resulting preferably in corresponding or comparable properties and advantages, even if the associated description is not repeated.

FIGS. 1 and 2 show a known nebulizer 1 for atomizing a fluid 2, particularly a highly effective pharmaceutical composition, medicament or the like, diagrammatically shown in a non-tensioned state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed or dispensed, which can be breathed in or inhaled by a user. Usually the inhaling is done at least once a day, more particularly several times a day, preferably at set intervals, depending on the complaint or illness from which a patient is suffering.

The nebulizer 1 is provided with or comprises an insertable or replaceable container 3 containing the fluid 2. The container 3 thus forms a reservoir for the fluid 2, which is to be nebulized. Preferably, the container 3 contains multiple doses of fluid 2 or active substance in particular sufficient to provide up to 200 dosage units or doses, for example, i.e. to allow up to 200 sprays or applications. A typical container 3, as disclosed in WO 96/06011 A1, holds e.g. a volume of about 2 to 20 ml.

Further, the number of doses contained in the container 3 and/or the total volume of the fluid 2 contained in the container 3 can vary depending on the fluid 2 or respective medicament and/or depending on the container 3 and/or depending on the necessary medication or the like.

Preferably, the container 3 can be replaced or exchanged, wherein the total number of uses of the nebulizer 1 and thus the number of containers 3, which can be used with the same nebulizer 1, is preferably restricted, e.g. to a total number of four or five containers 3. WO 2012/162305 A1 discloses additionally such a restriction to the total numbers of containers 3 which can be used with the same nebulizer 1.

The container 3 is preferably substantially cylindrical or cartridge-shaped and once the nebulizer 1 has been opened the container 3 can be inserted therein preferably from below and changed if desired. It is preferably of rigid construction, the fluid 2 in particular being held in a collapsible bag 4 in the container 3. In particular, the container 3 comprises a venting opening or hole 23 which is opened before or during first use.

The nebulizer 1 comprises a delivery mechanism, preferably a pressure generator 5, for conveying and nebulizing the fluid 2, particularly in a preset and optionally in an adjustable dosage amount.

The nebulizer 1 or pressure generator 5 comprises preferably a holder 6 for releasably holding the container 3, a drive spring 7 associated to the holder 6, only partly shown, and/or a blocking element 8 preferably in form of or with a button for preferably manual actuation or depressing. The blocking element 8 can catch and block the holder 6 and can be manually operated to release the holder 6 allowing drive spring 7 to expand.

The nebulizer 1 or pressure generator 5 comprises preferably a conveying element, such as a conveying tube 9, a non-return valve 10, a pressure chamber 11 and/or a nozzle 12 for nebulizing the fluid 2 into a mouthpiece 13.

The completely inserted container 3 is fixed or held in the nebulizer 1 via the holder 6 such that the conveying element fluidically connects the container 3 to the nebulizer 1 or pressure generator 5. Preferably, the conveying tube 9 penetrates into the container 3.

The nebulizer 1 or holder 6 is preferably constructed so that the container 3 can be exchanged.

When the drive spring 7 is axially tensioned in the tensioning process, the holder 6 with the container 3 and the conveying tube 9 are moved downwards in the drawings and fluid 2 is sucked out of the container 3 into the pressure chamber 11 of the pressure generator 5 through the non-return valve 10. In this state, the holder 6 is caught by the blocking element 8 so that the drive spring 7 is kept compressed. Then, the nebulizer 1 is in the tensioned state.

During the subsequent relaxation in the nebulization process after actuation or pressing of the blocking element 8 (either directly or by way of pressing an associated button 8b) the fluid 2 in the pressure chamber 11 is put under pressure as the conveying tube 9 with its now closed non-return valve 10 is moved back in the pressure chamber 11, here in the drawings upwards, by the relaxation or force of the drive spring 7 and now acts as a pressing ram or piston. This pressure forces the fluid 2 through the nozzle 12, whereupon it is nebulized into the aerosol 14, as shown in FIG. 1, and, thus, dispensed.

Generally, the nebulizer 1 operates with a spring pressure of 5 to 200 MPa, preferably 10 to 100 MPa on the fluid 2, and/or with a volume of fluid 2 delivered per stroke of 10 to 50 µl, preferably 10 to 20 µl, most preferably about 15 µl. The fluid 2 is converted into or nebulized as aerosol 14, the droplets of which have an aerodynamic diameter of up to 20 μm, preferably 3 to 10 μm. Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while an air supply can be sucked into the mouthpiece 13 through at least one optional air supply opening 15.

The nebulizer 1 comprises preferably a housing 24 and/or (upper) housing part 16 and optionally a biasing or inner part 17 preferably which is rotatable relative thereto (FIG. 2) and/or has an upper part 17*a* and a lower part 17*b* (FIG. 1).

The nebulizer 1 or housing 24 comprises preferably a (lower) housing part 18. This part 18 is in particular manually operable, and/or releasable fixed, particularly fitted or held onto the inner part 17, preferably by means of a retaining element 19.

Preferably, the housing parts 16 and 18 and/or other parts form the housing 24 of the nebulizer 1.

In order to insert and/or replace the container 3, preferably the housing 24 can be opened and/or the housing part 18 can be detached from the nebulizer 1, inner part 17 or housing 24.

Generally and preferably, the container 3 can be inserted before the housing 24 is closed and/or before the housing part 18 is connected to the housing 24. The container 3 may be inserted, opened and/or fluidically connected to the delivery mechanism automatically or simultaneously when (completely) connecting the housing part 18 to the housing 24/nebulizer 1 and/or when (completely) closing the housing 24/nebulizer 1. Preferably, the container 3 is open or fluidically connected when tensioning the nebulizer 1 for the first time with the current container 3.

Preferably, the nebulizer 1 or drive spring 7 can be manually activated or tensioned or loaded, in particular by actuation of an actuation member, here preferably by rotating housing part 18 or any other component.

The actuation member, preferably the housing part 18, can be actuated, here rotated relative to the upper housing part 16, carrying with it or driving the inner part 17. The inner part 17 acts on a gear or transmission to transform the rotation in an axial movement. As a result the drive spring 7 is tensioned in the axial direction by means of the gear or transmission (not shown) formed between the inner part 17, in particular its upper part 17*a*, and the holder 6 and acting on the holder 6. During tensioning the container 3 is moved axially downwards until the container 3 assumes an end position as shown in FIG. 2. In this activated or tensioned state the drive spring 7 is under tension and can be caught or held by the blocking element 8. During the nebulizing process the container 3 is moved back into its original position (non-tensioned position or state shown in FIG. 1) by (the force of) the drive spring 7. Thus the container 3 executes a lifting or stroke movement during the tensioning process and during the nebulizing process.

The housing part 18 preferably forms a cap-like lower housing part and/or fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal or foil 50 thereon with a piercing element 22 when the container 3 makes contact with it for the first time, to allow air in or aeration, preferably by opening or piercing venting hole 23. The venting hole 23 allows for pressure compensation inside the container 3 when fluid 2 is drawn from the container 3 during the actuation of the nebulizer 1.

The nebulizer 1 comprises preferably an indicator device 25, which counts in particular actuations of the nebulizer 1, preferably by detecting its tensioning or the rotation of the inner part 17 relative to the upper part 16 or housing 24. Preferably, the indicator device 25 or an associated locking device 26 locks the nebulizer 1 against (further) actuation or use, e.g. blocks further rotation of the housing part 18/inner part 17 and, thus, tensioning of the nebulizer 1 or its drive spring 7 and/or blocks actuation of the blocking element 8, in a locked state when a certain number of actuations or operations or discharged doses has been reached or exceeded.

In the following and with reference to the further figures, a preferred embodiment of the nebulizer 1, container 3, indicator device 25 and/or locking device 26 is described and shown according to the invention, wherein primarily important aspects and differences will be described and the previous aspects, features and explanations apply preferably additionally or correspondingly even without repetition.

FIG. 3 shows the nebulizer 1 with the container 3 and indicator device 25 according the present invention in a schematic section (longitudinal section) in the nontensioned state with completely closed nebulizer housing 24 and, thus, closed housing part 18, wherein the container 3 including the proposed indicator device 25 are inserted into or received within the nebulizer 1 and/or housing 24.

FIG. 4 shows an enlarged partial section of the encircled part of FIG. 3 in the non-tensioned state of the nebulizer 1. FIG. 7 shows a perspective section of the indicator device 25 in its initial (non-actuated) state, i.e. a state the indicator device 25 is initially in when the nebulizer 1 is in its non-tensioned state (the container 3 and nebulizer 1 is omitted in FIG. 7).

FIG. 5*a* shows the nebulizer 1 with container 3 and indicator device 25 in the same schematic section as FIG. 3, but in the tensioned state. FIG. 5*b* shows the same enlarged partial section as FIG. 4, but in the tensioned (but unlocked) state with completely closed housing 24. FIG. 8 shows a similar perspective section of the indicator device 25 as FIG. 7, but in the actuated state and also showing the engagement of the indicator device 25 with the housing part 18 of the nebulizer 1 in the tensioned state of the nebulizer 1.

The nebulizer 1 has preferably a longitudinal form or axis which corresponds to the axial direction and/or to the main dispensing direction and/or to stroke movement of the container 3 during tensioning and dispensing.

In the shown non-tensioned state (FIG. 3, FIG. 4), the nebulizer 1 or its mouthpiece 13 is preferably closed by a mouthpiece cover 27. The mouthpiece cover 27 is preferably pivotable to allow opening of the mouthpiece 13 for using the nebulizer 1.

Preferably, the indicator device 25 is directly and/or unreleasably secured or fixed to or connected with the container 3. In particular, the indicator device 25 is associated to a respective container 3. If the container 3 of the nebulizer 1 is replaced, the indicator device 25 is necessarily or positively replaced as well.

Preferably, the indicator device 25 is fixedly arranged at the bottom or container base 21 of the container 3 and/or opposite to an outlet or head 28 of the container 3.

In the present embodiment, the indicator device 25 is preferably directly connected to or abuts at an outer case or preferably rigid housing 29 of the container 3.

Preferably, the indicator device 25 and the container 3 are connected by form-fit and/or snap-fit.

In particular, the indicator device 25 circumvents and/or grips over a (lower or bottom) edge 30 and/or any other protrusion or the like of the container 3. In the present embodiment, the edge 30 is a little bit wider in diameter so that it protrudes radially over the essentially cylindrical outer form of the side wall of the container 3/container housing 29.

The diameter of the indicator device 25 is preferably at least essentially equal to or slightly greater than the diameter of the container 3 or its edge 30.

The edge 30 is preferably formed between the side wall and the bottom or base 21 of the container 3 or container housing 29. Preferably, the edge 30 is formed by flanging, bordering, bending or crimping or by any other suitable material-deforming process.

The indicator device 25 comprises a housing 31 and/or preferably has an at least essentially cylindrical form.

The indicator device 25 or its housing 31 is preferably attached to the container 3 or its base 21 or housing 29 with an at least essentially flat and/or axial side.

The indicator device 25 or its housing 31 comprises preferably a holding or gripping section 32 for connecting the indicator device 25 with the container 3. Preferably, the gripping section 32 circumvents the edge 30 and/or grips around or over the edge 30.

In the present embodiments, the gripping section 32 is preferably annular and/or grips over the edge 31 at positions distributed over the circumference of the edge 30 or container 3.

Preferably, the indicator device 25 and the container 3 are connected with each other by a snap-fit or click connection or by a form-fit and/or a force fit or by an adhesive bond. Preferably, the container 3 and the indicator device 25 are connected with each other by axially snapping one part on the other.

Preferably, the gripping section 32 is sufficiently elastic in radial direction so that the container 3 can be entered axially with its edge 30. For this, the gripping section 32 preferably comprises a respectively inclined insertion face to facilitate insertion of edge 30 into the annular gripping section 32 or between circumferentially distributed gripping sections 32.

Alternatively, the gripping section 32 may be formed by a part separate to the indicator housing 31 and may be connected to the indicator device 25 when the container 3 is attached to the indicator device 25. The part forming the gripping section 32 then preferably holds the container 3 in a press-fit on the indicator device and is connected to the indicator housing 31 preferably along an outer contour or circumference, preferably by snap-fit or click connection or by form-fit and/or force fit.

It has to be noted that other constructional solutions are possible for connecting the container 3 or its housing 29 with the indicator device 25 or its housing 31 or vice versa. In particular, the two parts can be connected with each other additionally or alternatively by welding, brazing, gluing, screwing, clamping, hot-pressing, or the like.

FIG. 6 shows in a schematic, exploded view the indicator device 25 according to the preferred embodiment of the present invention.

The indicator comprises a housing 31 and optionally an upper part 33 preferably attached to the housing 31.

Preferably, the upper part 33 holds or forms the gripping section 32.

The indicator device 25 comprises preferably an indicator element 35 and an actuation element 36. Preferably the indicator device 25 comprises a transmission 40 and preferably also a gear 41 for indexing the indicator element 35 or for causing the indexing of the indicator element 35.

The indicator device 25 is for counting and/or indicating a number of uses performed or still possible with the respective or associated container 3. Preferably, the indicator element 35 comprises markings **35*b*, such as one or more symbols, numbers, colored or shaded areas or the like, for at least roughly indicating the number of uses already performed with or still possible with the respective container 3. In the present embodiment, the indicator element 35 is preferably rotatable and/or comprises a circumferential wall or outer surface with the at least one marking 35*b***.

The indicator housing 31 comprises preferably a window **31*a*, in particular in the circumferential wall through the relevant marking 35*b* is visible for a user or patient, preferably through the housing part 18** which is in particular transparent.

The actuation element 36 comprises preferably an actuation arm or a guide element **36*a* for direct or indirect actuation or indexing of the indicator element 35. Indexing means that the indicator element 35** is moved forward in increments or steps.

Preferred is an indirect actuation or driving so that the actuation element 36 or its arm or guide element **36*a* actuates or drives the indicator element 35 via a transmission 40. In the present embodiment, the actuation element 36 drives the transmission 40 indirectly via an advancing element 39 which drives the transmission 40. Preferably, the transmission 40 has an associated gear 41** which results in a reduction.

Preferably, the actuation element 36 indirectly causes a rotation of the transmission 40 around an axis preferably parallel to the direction of movement of the actuation element 36. Preferably, the transmission 40 can rotate around an axis which is identical or coaxially aligned with the axis around which the advancing element 39 and/or the indicator element 35 can rotate.

Preferably, the actuation element 36 is movable along or parallel to the longitudinal axis of the indicator device 25 and/or nebulizer 1. For actuation of the indicator device 25, the actuation element 36 is preferably moved by interaction with the nebulizer 1 upon usage of the nebulizer such as tensioning or actuation of the nebulizer 1 or pressurizing or dispensing formulation in or from the nebulizer 1. Preferably, for actuation of the indicator device 25, an engagement of a part of the nebulizer 1 (or housing part 18) and the actuation element 36 occurs along or parallel to the longitudinal axis of the nebulizer 1.

Preferably, the axial or longitudinal actuation movement for actuating the indicator device 25 is converted into a radial or rotational movement inside the indicator device 25. Preferably, the indicator device 25 comprises a guide track **39*a* and/or an inclined plane and an associated guide element 36*a* for converting an axial movement into a rotary movement for driving the counting ring or an associated gearwheel or transmission 40 and/or gear 41. This allows driving the indicator device or counting without any elastic deformation of the actuation element 36** and thus a construction which is particularly reliable in operation.

In particular, the actuation element 36 of the preferred embodiment of the indicator device 25 comprises at least one guide element 36, in particular two guide elements 36a arranged on opposite sides. The guide elements 36a preferably extend radially outwards from the actuation element 36, particularly on opposite sides. The guide elements 36a are preferably constructed in the manner of pegs. Where reference is made hereinafter to only one guide element 36a, this is because a single guide element 36a is theoretically sufficient to perform the function, even though preferably two guide elements 36a will be provided on opposite sides for reasons of design, stability and/or safety. A part of the indicator device 25, in particular an advancing element 39, comprises at least one, preferably two guide tracks 39a and/or inclined planes for engagement with the guide element(s) 36a. The guide elements 36a each preferably pass radially through their associated guide tracks 39a. The guide track(s) 39a or the inclined plane(s) preferably form as a slot or a groove in which the associated guide element 36a engages. The guide track(s) preferably comprises the inclined plane or an inclination, for example in a range of 30° to 60°. Particularly preferably, the guide track comprises (or the inclined plane is formed by) a helical track section.

Preferably, the actuation element 36 is only moveable in axial/longitudinal direction (i.e. the actuation element is secured against rotation) and thus guide elements 36a are movable only in axial direction. In particular, the indicator housing 31 or a part of it, preferably the signal element 34 (as can be seen in FIG. 7) comprises an axially extending rib or groove 34b in which a corresponding groove or rib of the actuator element 36 is axially or longitudinally movable, wherein the engagement of the respective rib and groove prevents a relative rotation between the actuator element 36 and the indicator housing 31 and/or signal element 34.

Preferably, the advancing element 39 is only moveable radially or in a rotary movement. In particular, the advancing element 39 is held axially fixed in relation to the bottom of the indicator device 25 or indicator housing, most preferably the advancing element is axially held by the signal element 34. Preferably, the signal element 34 comprises a clip 34c which grips onto a radial shoulder of the advancing element 39 (the clip 34c can be seen in FIG. 12), whereby the clip 34c connects the advancing element 39 axially with the signal element 34 but allows a relative rotational movement of the advancing element 39 or of the shoulder under the clip 34c. Preferably the clip 34c can be flexed radially inwards for mounting the advancing element 39 to the signal element 34.

When the indicator device 25 is actuated, the axial movement of the guide elements 36a (here: away from the bottom of the indicator device 25) takes place. In the course of the axial movement of the guide elements 36a, the advancing element 39 is forced into rotary movement due to the engagement between the guide element 36a and the inclined guide track 39a. The axial movement of the guide elements 36a pushes on the walls of the guide tracks 39a (or inclined planes) and thus pushes the advancing element 39 sidewise i.e. into rotary movement.). In particular, the advancing element 39 is rotated by an angular increment. The size of this angular increment depends on the inclination of the guide track 39a and the length of the axial movement of the actuation element 36. Preferably, the angular increment of the rotational movement or the angular increment of the advancing element is in the range of 5° to 20°, more preferably in the range of 10° to 16°. However, other constructional solutions are possible for the transfer of axial into rotary movement. For instance, actuation element 36 may comprised the guide tracks engaging with guide elements or pegs on the advancing element.

The actuation element 36 in its initial (or non-actuated) state is preferably axially supported by the indicator housing 31 or by a part complementing the indicator housing 31, particularly by the signal element 34. Preferably, the indicator device 25 comprises a part which supplies a guidance for the preferably longitudinal movement of the actuation element 36. In the shown embodiment, the actuation element 36 comprises a tube-like section or a section with an outer cylindrical wall wherein this section is moveable in a tube-like section of the transmission 40 (the transmission 40 thus forming the guidance for the actuation element 36). However, other constructional solutions are possible, as well.

The rotary movement of the advancing element 39 can directly or indirectly (with or without a gear transmission ratio differing from 1:1) be transferred to an indicator element 35 of the indicator device 25. Shown in FIG. 3-15 is a preferred embodiment with an indirect transfer of rotary movement and with a gear transmission ratio; however other constructional solutions are possible.

Preferably, the indicator device 25 comprises an actuation element 36, an advancing element 39, a transmission 40 and a ratchet element 37. However other constructional solutions are possible, in particular functions of different parts may be combined, if a direct advancement of an indicator element 35 and/or a 1:1 gear transmission ratio is sufficient (for instance if an indicator device with a comparatively small count range is to be designed).

FIG. 9 shows an assembly of selected interacting parts of the indicator device, in order to demonstrate the engagements of actuation element 36 and advancing element 39, of advancing element 39 and transmission 40 and of transmission 40 and ratchet element 37 for the embodiment shown in FIG. 3-15. Preferably, the advancing element 39 comprises means to engage with associated means on transmission 40. In particular, the advancing element 39 comprises at least one protrusion or tooth 39b (preferably two teeth) to engage with an associated recess or tooth on the transmission 40. Preferably, the associated recess or tooth on the transmission 40 is asymmetrical, in particular in form of saw teeth. Preferably, the engagement means on transmission 40 is a first set or array of saw teeth 40a. Preferably, the set of saw teeth 40a are circumferentially arranged on transmission 40 and/or facing in axial direction (in this case towards the bottom side of the indicator device 25). The at least one tooth 39b is preferably formed by an elastic or flexible arm 39c on the advancing element. Preferably, the advancing element is made of plastic. Preferably, the elastic or flexible arm or its end forming tooth 39b is biased towards transmission 40 (i.e. away from the bottom of the indicator device 25 in this case). Preferably, at least one tooth 39b is asymmetrical, in particular in form of a saw teeth.

Preferably, the saw teeth 40a are asymmetrical, i.e. comprise differently inclined shoulders on one side and the other side in order to facilitate and/or ensure the incremental actuation and movement in one rotational direction by the back and forth movement transferred from the actuation element 36.

The view shown in FIG. 9 is a partly sectional view as it contains a cut-out section C just for demonstration purpose of this figure only. In this cut-out section C, it can be seen how the tooth 39b which is preferably hold by or formed on a flexible arm 39c engages with the first set of saw teeth 40a on the lower side of transmission 40.

When the actuation element 36 is moved upwards (here: away from the bottom of the indicator device 25), the advancing element 39 is rotated (to the left in FIG. 9). The rotational movement of the advancing element 39 results in that the tooth 39b is rotated against the first set of saw teeth 40a on transmission 40. Preferably, tooth 39b is asymmetrical and comprises an abutment side and an inclined shoulder. Preferably, the associated first set or array of saw teeth 40a comprise differently inclined shoulders on alternating sides of the tips of the saw teeth, wherein in particular, one shoulder is inclined to form a ramp and the other shoulder forms an abutment for the abutment side of tooth 39b. Upon the (actuational) rotation of the advancing element 39, the abutment side of tooth 39a pushed against the abutment side of a saw tooth in the first set of saw teeth 40a and thus pushes the saw tooth and thus transmission 40 incrementally into the same rotational direction.

When the actuation element 36 is moved downwards (preferably biased particularly by a biasing spring 38), the advancing element 39 rotates back to its initial position (back-movement is to the right in FIG. 9). However, the construction of the engagement between the advancing element 39 and the transmission 40 prevents a (simultaneous) back-movement of the transmission 40: The tooth 39b is preferably formed by a flexible arm 39c which can be flexed away from the transmission 40 (here: downwards). When the advancing element 39 is moved back, a ramp on tooth 39b glides along a saw tooth inclination of the first set of saw teeth 40a. Hereby, the flexible arm 39c is flexed out. Any rotational back-movement of transmission 40 and thus any back-movement parts driven by transmission 40 (here: gear 41 and indicator element 35) is prevented.

Preferably (as in the shown embodiment), the forward movement (and preferably only the forward movement) of the container 3 and/or of the actuation element 36 actuates the indicator device 25 and/or is detected or counted, and the back movement of the container 3 and/or of the actuation element 36 does not result in any rotational displacements within the indicator device 25 and/or in any indexing.

The gear transmission ratio within the indicator device 25 may be designed or constructed such that a reduction and/or non-linear driving or indexing is achieved.

Preferably, the transmission 40 drives a gear 41 which drives the indicator element 35. Such a construction with multiple interacting driving parts enables presetting gear transmission ratio, in particular a reduced transmission and/or a non-linear transmission (Preferably, the indicator element 35 is only moved by multiple actuations of the indicator device 25, i.e. by multiple incremental step-wise rotation of transmission 40 in particular). In particular, an indicator device 25 according to the shown embodiments has a gear transmission ratio in the range of 1:1 to 10:1, more preferably a reduced transmission with a gear transmission ratio in the range of 2:1 to 4:1 for transferring the rotational movement of the advancing element 39 into a rotational movement of the indicator element 35.

FIGS. 10a and 10b show an assembly of selected interacting parts of the indicator device, in order to demonstrate the engagements of transmission 40 and gear 41 and of gear 41 and indicator housing 31 for the preferred embodiment of the indicator device 25 (shown in FIG. 3-15).

Preferably, the central component of the reduced transmission in the step-by-step indexing mechanism is an epicyclic gear, consisting of a planet wheel or gear 41, a sunwheel or gear ring 40b (preferably formed by transmission 40) which preferably rests on a disc (formed by transmission 40) that has teeth on its underside (first set of saw teeth 40a) and a gear rim 31b that cooperates with the planet wheel or gear 41. (However, other constructional solution to supply a gear transmission ratio differing from 1:1 are possible, as well). This gear rim 31b is formed on the inside of the wall of a preferably non-rotatably secured part of the indicator device 25, in particular on the inside of a wall of indicator housing 31. Preferably the gear rim 31b comprises an array of preferably circumferentially arranged recesses 31c or slots proceeding diagonally towards gear 41, wherein the slots open towards the edge of the gear rim 31b. Preferably, the recesses 31c form a saw teeth array towards gear 41. Preferably, two neighbouring recesses 31c form a teeth between them.

The sunwheel or gear ring 40b has coarse teeth or cogs. Thus, in the embodiment shown, six sunwheel teeth or gear ring cogs are preferably uniformly distributed over the circumference of the sunwheel or gear ring 40b. These sun-wheel teeth or cogs of gear ring 40b cooperate during the rotation of the sun-wheel/transmission 40 with the planet wheel or gear 41 that is arranged in the same plane between the sunwheel/gear ring 40b and the gear rim 31b of the indicator housing 31.

Preferably, the gear 41 is constructed as a cogwheel with multiple cogs 41b or teeth (preferably 3 to 8 cogs 41b). On one side of gear 41 (preferably on the side facing towards the inside of the indicator device 25), the teeth or cogs 41b of the gear 41 mesh with the teeth or cogs of the gear ring 40b on the transmission 40. On another side of gear 41 (preferably on the side facing towards the side wall of the indicator device 25), the teeth or cogs 41b of the gear 41 mesh with the teeth or recesses 31c preferably on the inside of the indicator housing 31. Preferably, these teeth or recesses 31c are multiply arranged in an array along an internal circumference of the indicator housing 31 and/or form the gear rim 31b. Preferably, always at least one cog 41b of the gear 41 engages in a recess 31c (or one teeth of the array of the teeth circumferentially arranged on the inside of the indicator housing 31 always engages between two cogs 41b of the gear 41).

When due to rotary movement of the transmission 40 a sunwheel teeth or gear ring cog abuts the next cog 41b of the planetwheel or gear 41, the planetwheel or gear 41 is stepwise rotated. Preferably, another cog 41b of the planetwheel or gear 41 simultaneously meshes with the gear rim 31b or the array of recesses 31c in the indicator housing 31. Preferably, the indicator housing and thus the gear rim 31b are secured against rotary movement and thus the enforced rotation of gear 41 (enforced by rotary steps of the planet wheel) forces the cogs 41b to move along gear rim 31b and/or forces gear 41 itself to move stepwise along gear rim 31b.

In the shown embodiment, the transmission 40 and the gear 41 are preferably constructed in such way that not every incremental rotation of the transmission 40 results in a movement of gear 41: only multiple incremental rotations of the transmission 40 result in one incremental rotation of gear 41 and thus in (at most) one incremental rotation of the indicator element 35 (i.e. the transmission is preferably non-linear). The necessary number of incremental rotations of the transmission 40 is defined or preset by the construction/form of transmission 40, gear 41 and recesses 31b in the indicator housing 31. As a rotation of gear 41 is transformed in a rotation of the indicator element 35, a pre-defined number of movements of the actuation element 36 from the first to the second position results in a movement of the indicator element 35.

The transmission properties of the epicyclic gear are not only dependent on the number of cogs 41b on the gear 41 or on the number and/or spacing of cogs on the sunwheel/gear ring 40b, but additionally the gear has transmission ratio (preferably resulting in a reduced transmission) which is dependent on a number of variables, for instance on the involved diameters like the diameter of the circle along which the recesses 31b are arranged, the diameter of the sunwheel/gear ring 40b and the size of the teeth of the first set of saw teeth 40a and/or the size of teeth 39b on the advancing element 39. Due to small variations in these variables the gear transmission ratio can be varied also slightly, so that non-whole-number-ratios can be preset (for instance gear transmission ratios of 2,5 or 3,15 can be preset). Thus an initial rotary movement of the advancing element 39 preferably results in a smaller rotary movement of the indicator element 35 (so that the markings 35b along the circumference of the indicator element 35 can indicate a larger overall number of counts). For instance, a rotary movement of the advancing element 39 of 15° may be reduced to a rotary movement of 5° of the indicator element 35).

Preferably, the indicator housing 31 is non-rotationally fixed to the container 3. Preferably, the rotation of the gear 41 around its preferably parallel axis results in a movement of gear 41 along the array of recesses 31b along the internal circumference of the indicator housing 31.

Preferably, the gear 41 is rotatably held by the indicator element 35. Preferably, gear 41 can rotate around an axis which is parallel to the axis around which the transmission 40 can rotate.

The planet wheel or gear 41 preferably comprises an axial pin or axle section 41a that preferably projects upwards on one side, i.e. away from the disc formed by transmission 40/away from the plane of the sunwheel/gear ring 40b. Preferably, this axle section 41a is rotatably held in a bore or bearing 35a in the indicator element 35. Thus, a permanent engagement between the gear 41 and the indicator element 35 is ensured. However, other constructional solutions or couplings between the gear 41 and the indicator element 35 are possible.

Preferably, the indicator element 35 which holds the gear 41 is moved simultaneously with a movement of gear 41 along a (internal) circumference of the indicator housing (this refers also to step-wise i.e. merely partial movement along the circumference), i.e. by moving gear 41 stepwise along gear rim 31b the indicator element 35 is likewise moved. Preferably, the gear rim 31b is arranged circumferentially and thus the indicator element 35 is rotated about the central axis of the circumferences on which the recesses 31c/the gear rim 31b is arranged. Preferably, the rotation of the gear 41 results in a rotation of the indicator element 35 around its preferably longitudinally oriented rotation axis.

However, other constructional solutions are possible as well. For instance, alternatively the gear 41 can be hold in a bearing on a non-movable component as for instance the indicator housing 31 and directly mesh with teeth or the like on a circumference of the indicator element 35.

Preferably, the indicator device 25 comprises a ratchet preventing any counter-rotation of the transmission 40 or gear 41.

Preferably, any back movement of the indication element or of the parts of the epicyclic gear is prevented. In the shown embodiment, this is achieved by means of a ratchet element 37 and/or the construction of the engagement between the rotationally movable parts in the indicator device 25.

In the present embodiment, the indicator device 25 comprises a ratchet element 37 that engages with the transmission 40 in such a way that the transmission 40 can rotate only in one rotational direction (preferably only during the container movement associated with the tensioning of the drive spring 7) and/or in such a way that the rotation of transmission 40 in one rotational direction (i.e. in the counter direction) is prevented (regarding the shown embodiment, preferably all discussed rotational movements are around an axis which is identical to the main longitudinal axis of the indicator device 25 and/or of the nebulizer 1).

Preferably, the ratchet element 37 comprises a pawl or latching arm 37a engaging with associated protrusions and/or recesses on the transmission 40 (see also FIG. 9 for the interaction of transmission 40 and ratchet element 37). Preferably, these protrusions and/or recesses are arranged in an array. Preferably, this array is a saw-teeth-arrangement (in particular, the second set of saw teeth 40c in the present embodiment as shown in FIGS. 6 and 9) and/or arranged circumferentially on the transmission 40. Even more preferably, the tip of the latching arm 37a points inwards (i.e. towards the central longitudinal axis of the indicator device 25) and/or is biased inwards and the associated saw-teeth (the second set of saw teeth 40c) are arranged on the outside of a tubular section 40d on the transmission 40 (wherein preferably, the transmission 40 and ratchet element 37 are arranged in such way in the indicator device that the tubular section 40d reaches through a central opening in the ratchet element 37). Alternatively, the ratchet may be formed by a flexible arm extending from another part of the indicator device 25, for instance from the housing 31 engaging with transmission 40 and/or meshing with or engaging into the gear 41 or its teeth 41b.

The rotational movement of the transmission 40 (here upon rotational movement of advancing element 39) results in that the second set of saw teeth 40c is rotated against the latching arm 37a (The ratchet element 37 is preferably not rotationally movable in the indicator device 25). Hereby, the latching arm 37a is flexed out. Preferably, associated protrusions and/or recesses on the transmission 40 are asymmetrical (preferably in form of saw teeth, i.e. forming said second set of saw teeth 40c), i.e. comprise differently inclined shoulders on alternating sides of the protrusions or recesses. One shoulder is inclined to form a ramp along which the latching arm 37a can be flexed outwards (during rotational movement of transmission 40 upon actuation of the indicator device 25) and the other shoulder forms an abutment for the tip of the latching arm 37a (so that any rotational back-movement of transmission 40 and thus any back-movement of gear 41 and indicator element 35 is prevented).

FIG. 7 shows the indicator device 25 in a perspective section in the initial, first position and resting-state (initial state: non-actuated and non-tensioned). FIG. 8 shows the indicator device 25 in a similar perspective section, but in an actuated state, i.e. with actuated actuation element 36.

FIG. 5 shows in a partial enlargement similar to the enlarged section shown in FIG. 4 a lower portion of the nebulizer 1 in a state after fully tensioning (tensioned state). The indicator device 25 is in an actuated state as also shown in FIG. 8.

The nebulizer 1 or housing part 18 comprises preferably a driving part 52 for driving or actuating the indicator device 25 when using the nebulizer 1, in particular for actuating the indicator device 25 in response to any tensioning of the nebulizer 1 and/or any (axial or stroke-like) movement of the container 3.

Preferably, the driving part 52 is arranged or formed in the housing part 18, in particular on the axial end face or bottom 53 of the housing part 18.

Preferably, the driving part 52 is arranged centrally and/or extends axially.

Preferably, the driving part 52 is at least substantially cylindrical and/or pin-like or bolt-like.

Preferably, the driving part 52 is held by the housing part 18 and/or integrally formed by the housing part 18.

In the preferred embodiment, the movement of the container 3 and, thus, of the indicator device 25 during the tensioning (downward movement in the drawings) and/or during pressurization and dispensing (upward movement in the drawings) and/or one or both of the respective end positions in the non-tensioned state and tensioned state, respectively, can be used for actuating the indicator device 25, i.e. for counting.

Preferably, the relative movement of the container 3 and/or indicator device 25 within the nebulizer 1, and more preferred the movement during tensioning, is used for actuating or triggering the indicator device 25 and/or counting.

When tensioning the nebulizer 1 and/or moving the indicator device 25 downwards, the driving part 52 enters or engages through an insertion opening 54 of the indicator device 25 or its housing 31, in particular axially.

Preferably, the driving part 52 and the insertion opening 54 are arranged centrally and/or axially aligned.

Preferably, the actuation element 36 is actuated by means of the driving part 52 that enters an insertion opening 54 of the indicator device 25. Preferably, the driving part 52 contacts the actuation element 36 at an actuation surface **36*c* of the when the driving part 52 actuates the actuation element and/or indicator device 25**.

Preferably, the driving part 52 moves the actuation element 36 away from the insertion opening 54 and/or towards the container 3.

Preferably, during the tensioning process of the nebulizer 1 the container 3 with the attached indicator device 25 is moved towards the bottom 53 of the nebulizer and/or towards the driving part 52, so that the insertion opening 54 is pushed over the driving part 52. Thus the driving part 52 enters the indicator device 25 via the insertion opening 54, until the fully tensioned state of the nebulizer is reached (as shown in FIG. 8). In the initial state the tip of the driving part 52 may or may not protrude into the insertion opening 54 of the indicator device 25 (this may depend on the tolerances in the height of various involved components). However, in the initial (non-tensioned) state, the tip of the driving part 52 preferably does not contact the actuation surface **36*c* of the actuation element 36**.

Preferably, the actuation element 36 comprises a hollow cylindrical structure in which an internally protruding rim or flat forms the actuation surface **36*c*. During the tensioning process the driving part 52 contacts the actuation surface 36*c* of the actuation element 36 (preferably reaching into the hollow cylindrical structure of the actuation element 36) and pushes it towards the container 3 (i.e. upwards in FIG. 7) and/or transferring the relative axial movement between indicator device 25 and driving part 52 into a relative axial movement inside the indicator device, in particular into a relative axial movement between the actuator element and the indicator housing/the advancing element 39** etc. which results in actuating the counting in the indicator device.

In the present embodiment, the driving part 52 actuates the actuation element 36, i.e. moves the actuation element 36 from an initial first position shown in FIGS. 3, 4 and 7, to an actuated second position shown in FIGS. 5 and 8.

Preferably, the actuation element 36 is linearly moveable and/or forms a sliding carriage.

Preferably, the actuation element 36 is supported and/or held moveably by the housing 31 or by a signal element 34 forming a lower part of the housing 31. However, other constructional solutions are possible as well.

Although the figures only show an embodiment in which the actuation of the indicator device 25 occurs upon the tensioning of the nebulizer 1, the indicator device 25 and its rotationally movable parts may alternatively be constructed in such way that only the back movement of the container 3 and/or of the actuation element 36, i.e. the movement of the container 3 upon the relaxation of the drive spring 7, actuates the indicator device 25 or gear 41 and/or is detected or counted. The triggering of the counting or actuation of the transmission 40/gear 41 would then be effected by the pressurization or dispensing process or movement, i.e. during the actual dispensing of fluid 2, i.e. usually during actual use or inhalation. In such an alternative (not shown) embodiment, the engagement between the rotationally movable parts in the indicator device may be designed in such a way that all the contact sides for the arm of the ratchet element 37 and saw teeth arrays are turned into the opposite rotational direction compared to the embodiment shown in FIGS. 6, 9 and 10. Thus, the actuation element 36 or its guide elements **36*a* may transmit the movement from the second to the first position to the transmission 40 and this movement may cause an incremental rotation of gear 41**.

Also in such an alternative embodiment, the actuation element 36 may be moveable back and forth between the first and second positions for (preferably indirectly) indexing the indicator element 35, in particular for incrementally rotating the transmission 40 and thus rotating gear 41 via the advancing element 39 to respectively drive the indicator element 35. (Alternatively, in particular if every actuation of the actuation element 36 is to induce a stepwise movement and/or preferably unreduced rotational movement of the indicator element 35, the indicator element 35 may also here be driven directly by the advancing element 39 without using transmission 40 and gear 41 as separate parts).

The transmission 40 or gear 41 may also transform the movement of the advancing element 39, into an indexing of the indicator element 35. Preferably, the indicator device 25 may also have a gear transmission ratio or the transmission function of the transmission 40 and/or gear 41 is designed or constructed such that a reduction or non-linear driving or indexing is achieved.

Preferably, only either forward (as in the shown embodiment) or backwards movement of the container 3 and/or of the actuation element 36 actuates the indicator device 25 and/or is detected or counted, i.e. results in step-by-step counting movements within the indicator device 25.

In the present embodiment, the actuation element 36 is moveable parallel or coaxially to the longitudinal or dispensing direction of the container 3 or nebulizer 1 and/or to the stroke movement of the container 3 and/or indicator device 25.

Preferably, the actuation element 36 is moved from the more outer, first position axially inwards to the second position. In the second position, the actuation element 36 with its actuation arm or guide element **36*a* has moved the advancing element 39** from a first radial position into a second radial position.

The indicator device 25 comprises preferably a biasing spring 38, in particular for biasing the actuation element 36 into a preferred direction.

In particular, (preferably upon actuation) the actuation element 36 is moved against the force of the associated, preferably helical, biasing spring 38 biasing the actuation element 36 in opposite direction.

When the actuation element 36 is moved from the first position to the second position, the actuation element is in particular moved against the force of the associated, preferably helical, biasing spring 38.

Preferably, the biasing spring 38 biases the actuation element 36 towards the bottom of the indicator device 25 (i.e. away from the container side of the indicator device 25) and/or towards an insertion opening 54 (downwards in FIGS. 3 to 8, 12, 13 and 15).

Preferably, the biasing spring 38 biases the actuation element 36 into the first position (i.e. into the initial position, which the indicator device 25 preferably has in the non-tensioned state of the nebulizer 1).

Preferably, the actuation element 36 and/or a support structure 36b formed by the actuation element 36 supports or holds the biasing spring 38. Preferably, the biasing spring 38 abuts the indicator housing 31 or the upper part 33 (of the indicator device 25) or the container housing 29 or the container base 21 or a foil 50 covering the container base (or any other feature at the bottom of the container 3).

In the (fully) tensioned state, the container 3, more precisely the aeration opening or venting hole 23, is opened at least when the nebulizer 1 is tensioned with a container 3 for the first time.

Preferably, the opening of the container 3 or venting hole 23 for aeration is realized by piercing or breaking, in particular of foil 50.

The opening or piercing can be effected directly by the driving part 52. Alternatively, the opening or piercing can be effected independently from the driving part 52, e.g. by means of the aeration spring 20 with the piercing element 22 similar to the embodiment shown in FIG. 2. Alternatively, as in the present embodiment, the opening or piercing can be achieved indirectly, preferably via the piercing part 48 which is preferably actuated by the driving part 52.

Preferably, the piercing part 48 is formed as separate part and/or provided by the indicator device 25 and/or arranged within the indicator device 25.

The indicator device 25 comprises preferably a piercing part 48, preferably with a piercing tip 49 (compare FIGS. 3 to 8).

The piercing part 48 is arranged within the indicator device 25 or its housing 31.

The piercing part 48 is preferably axially moveable.

The piercing part 48 is preferably moveable such that it can protrude towards the container 3 and/or can open an aeration opening, preferably the venting hole 23, of the container 3, in particular by breaking or piercing a foil 50 covering the venting hole 23.

In the present embodiment, the piecing element 48 comprises preferably an opening end or tip 49 which can open or pierce the foil 50 covering the container base 21, in particular an indention 51 formed in the container 3 or its base 21. Preferably, the indention 51 comprises a breakthrough which forms the venting hole 23. However, other constructional solutions are possible as well.

Preferably, the piercing part 48 is preferably held axially moveable by a support structure 36b of the indicator device 25, housing 31, actuation element 36 and/or indicator element 35.

It has to be noted that the piercing part 48 or its tip 49 is preferably received within the indicator device 25 or its housing 31, but can protrude outwards in the actuated state.

Preferably, the piercing part 48 is supported or fixed to or formed by the actuation element 36. Preferably, the piercing part 48 is axially moved when the step-by-step indexing mechanism within the indicator device 25 and/or when the counting in the indicator device 25 is actuated.

In the preferred embodiment as schematically indicated in FIGS. 4 and 5, the piercing part 48 is particularly held by a support structure 36b formed by the actuation member 36 and is axially movable together with the actuation element 36. Thus the piercing part 48 is preferably moved towards the container 3 upon actuation of the indicator device 25, preferably durunring the tensioning process of the nebulizer 1. Thus the piercing element 48 preferably is in a piercing position i.e. in a state in which it pierces foil 50 and or opens the aeration of container 3.

The piercing part 48 is preferably constructed as separate, part, which is optionally directly or indirectly spring biased in the longitudinal or axial direction away from the container 3, so that the piercing tip 49 is retracted from the container 3 in the non-tensioned state. In the shown embodiment the piercing part 48 is indirectly biased away from the container 3 as a result of the biasing spring 38 acting on the actuation member 36 (wherein the piercing part 48 is preferably fixed to the actuation element 36). Thus the piercing part 48 is retracted from its piercing position at the container base 21 when the actuation element 36 moves back from its second (actuated) position to its first (initial) position, i.e. preferably upon dispensing when the nebulizer 1 returns from its tensioned state into its non-tensioned state.

The opening or piercing can be repeated each time the nebulizer 1 is tensioned, i.e. each time when the container 3 reaches its end position in the tensioned state.

Preferably, the piercing part 48 comprises a compensation portion, such as a flexible structure, or is at least partly compressible for compensating any tolerances in axial direction. Such tolerances can occur in particular due to variations during production, in particular variations of the length of the container 3 and/or other components, variations of the connection of the container 3 with the indicator device 25, variations of the length of the indicator device 25 or its housing 31, variations of the axial position of the container 3 within the holder 6, and the like. Thus different distances between the free end of driving part 52 and the counterface of the piercing part 48 or the actuation element (which supports the piercing part) can result. The construction is such that the driving part 52 and the piercing element 22 cooperate in any case such that the desired piercing is ensured.

The compensation portion or the compressibility allows axial compression when a predetermined axial force is exceeded in order to avoid any damage of the container 3 and/or any other component of the nebulizer 1.

Thus, in the preferred embodiment the driving part 52 first moves the piercing part 48 towards the container base 21 into the piercing position and further axial movement of the driving part 52 is compensated by the compensation portion or the compressibility of the piercing part 48.

In the shown embodiment, the piercing part 48 is preferably formed by a helical spring and the compensation is given by the axial compressibility of the spring coils. Preferably, the helical spring comprises or consists of a preferably metallic wire. In particular, one end of the wire is bend and/or shaped/grinded into a central tip which forms the piercing tip 49 which points towards the container base 21. Preferably, the end of the wire forming the piercing tip 49 comprises at least one bevel (for instance formed by cutting or grinding) ending in a point-like tip.

In an alternative (not shown) embodiment, the piercing part 48 and the actuation element 36 are a one-piece-construction, preferably made of plastic in an injection molding process.

Preferably in the alternative embodiment, the support structure 36a may comprise flexible arms or ribs for holding the piercing part 48. The flexible arms or ribs form a compensation portion for compensating any tolerances in axial direction. The compensation portion allows axial compression when a predetermined axial force is exceeded in order to avoid any damage of the container 3 and/or any other component of the nebulizer 1. Thus, in the alternative embodiment the driving part 52 first moves the piercing part 48 towards the container base 21 into the piercing position and further axial movement of the driving part 52 is compensated by the compensation portion, preferably by the flexible arms 56 being spread radially outwards. The piercing part 48 may be biased into its retracted or initial position, in particular by a preferably integrally formed biasing arm, spring or the like, preferably by the support structure 36b.

In the (fully) tensioned state (as shown in FIG. 5 and FIG. 8) the nebulizer 1 is ready for dispensing which is preferably initiated by starting the relaxation of the drive spring 7 (by pressing the blocking element 8 in the current embodiment). Upon starting the relaxation of the drive spring 7, i.e. during the pressurization or dispensing process, the container 3 moves upwards again (until reaches its position shown in FIGS. 3 and 4 again). During this process, the driving part 52 is withdrawn from the indicator device 25 or through the insertion opening 54 such that the actuation element 36 starts to return to its initial or first position due to the force of the biasing spring 38. Finally, after sufficient withdrawal of the driving part 52, the actuation element 36 returns into the first position shown in FIGS. 3 and 4 when the back movement is completed. In the end position, i.e. in the non-tensioned state, the driving part 52 is preferably further or completely retracted from the indicator device 25, the indicator housing 31 and/or insertion opening 54 as shown in FIGS. 3 and 4.

After the number of uses of the nebulizer 1 with the container 3 has reached or exceeded a predetermined number of uses as detected or registered by the indicator device 25, a locked state is entered and the nebulizer 1 will be locked against further use with the current container 3 and/or the container 3 will be locked against further use with the nebulizer 1. Preferably, during the last dispensing or pressurization process, the indicator device 25 has moved the indicator element 35 one step further and detected or registered that the predetermined number of uses has been reached or exceeded and, thus, that the locked state shall be entered.

Preferably, the indicator device 25 comprises a signal element 34 or flag which becomes visible or more visible to the user of the nebulizer 1 when the locked state of the indicator device 25 is entered. Preferably, an enlarged visibility of the signal element 34 in the locked state of the indicator device 25 shows the user of the nebulizer 1 (preferably additionally to a reading of the markings 35b through the window 31a of the indicator housing 31) that the predetermined number of uses of the nebulizer 1 with the container 3 associated to this indicator device 25 in its locked state has been reached or exceeded and/or that the container 3 is empty. Preferably, the signal element 34 or a visible part of it has a signal colour like red and/or a colour which enhances the visibility of the signal element 34. Preferably, the signal element 34 has a cylindrical wall 34w that in particular has a signal colour.

Preferably, in the locked state of the indicator device 25 a signal element 34 protrudes from the indicator device 25 (on the bottom side). In particular, the cylindrical wall 34w is visible at least for the most part in the locked state of the indicator device 25. Preferably, the locked state of the indicator device causes or effects a locked state of the nebulizer 1, particularly causes or effects a blocking of the tensioning/actuation of the nebulizer 1.

Preferably, the indicator device 25 comprises a blocking part which is actuated when the locked state of the indicator device 25 is entered.

Preferably, the signal element 34 forms the blocking part (or is identical with the blocking part) of the indicator device or is part of the blocking part. However, other constructional (not shown) solutions are possible wherein the signal element and the blocking part are different parts of the indicator device and/or are actuated independently of each other.

Preferably, the blocking part/signal element 34 is integrated into the indicator device 25 or its housing 31.

The blocking part/signal element is preferably moveable parallel to the longitudinal or dispensing direction of the container or nebulizer 1 and/or of the direction of stroke movement of the container 3.

Preferably, the blocking part/signal element 34 is linearly moveable and/or formed by a sliding carriage. However, other constructional solutions are possible as well.

Preferably, the signal element 34/blocking part disables the interaction of the driving part 52 and the indicator device 25 after the last dose of fluid 2 has been dispensed and when the locked state has been entered or detected.

Preferably, the signal element 34/blocking part prevents a contact of the driving part 52 and the actuation element 36. In particular, the signal element 34 prevents further actuation of the counting mechanism of the indicator device 25.

Preferably, the signal element 34/blocking part is biased into its signaling/blocking position, in the present embodiment preferably by actuation spring 47 or any other suitable biasing means.

The actuation spring 47 acts preferably between the housing 31 one hand and the signal element 34/blocking part on the other hand.

Preferably, the indicator housing 31 has (at least partly) a double-wall construction, i.e. comprises an outer wall 31o and an inner wall 31i. Preferably, the actuation spring 47 is arranged between the outer wall 31o and the inner wall 31i of the indicator housing 31. Preferably, the wall 34w of the signal element 34 is at least for the most part arranged inside the inner wall 31i and/or between the outer wall 31o and the inner wall 31i of the indicator housing 31 in the initial state of the indicator device 25 (see FIG. 8). Preferably, the actuation spring 47 is arranged between the wall 34w of the signal element 34 and the inner wall 31i of the indicator housing 31.

In the present embodiment, the spring 47 is preferably compressed in a first position (in the unlocked state of the indicator device 25) and biases the signal element 34/blocking part towards a second position which the signal element 34/blocking part assumes in the locked state of the indicator device 25. In the second position (as shown in FIGS. 12, 13 and 15), the signal element 34/blocking part enlarges the longitudinal extent or height of the indicator device 25 and/extends from the indicator housing 31.

In particular, the signal element 34 in its second position restricts the axial moveability of the container 3 in the nebulizer 1 and thus acts as a blocking part blocking further use of the container 3 as will later be explained in more detail.

Preferably, the actuation element 36 is held in such way in the indicator device 25 that it is not moved in the same extend towards the bottom 53 of the nebulizer 1 as the signal element 34, i.e. preferably, the axial movement of the actuator element 36 is not only restricted by the signal element 34. For instance (in an alternative not shown in the figures), the actuator element 36 may be connected to the biasing spring 38 preferably by snap-fit at one end of the biasing spring and the other end of the biasing spring 38 may be connected preferably by snap-fit to another part of the indicator device 25, for instance to the upper part 33 or to the ratchet element 37.

Preferably, in the second position the signal element 34/blocking part enlarges the distance between the insertion opening 54 and an actuation surface 36c (on the actuation element 36) corresponding to (or in the unlocked, tensioned state interacting with) the driving part 52. Thus (for an embodiment in which the actuator element 36 does not or does not fully follow the axial movement of the signal element from the first to second position), in the locked state of the indication device 25, the height of the driving part 52 is not sufficient anymore to abut (i.e. interact with) the actuation surface 36c of the actuation element 36 upon tensioning of the nebulizer 1. Preferably, the longitudinal height of the signal element 34/blocking part or the partial height of the signal element 34 as far as it extends from the indicator housing 31 in the locked state of the indicator device 25 is larger than the height of the driving part 52 and/or is larger than the distance the container 3 travels in a full tensioning process.

Preferably, in the locked state of the indicator device 25 the bottom of the indicator device 25 or bottom 34a of the signal element 34/blocking part abuts the bottom 53 of the nebulizer 1 during the tensioning process, before the driving part 52 touches the actuation surface 36c of the actuation element 36. Thus no force is extorted on driving part 52 during the tensioning process involving an indicator device 25 in the locked state.

In particular, the signal element 34 acts as a blocking part of the indicator device 25 wherein the signal element 34 blocks further use of the container 3 and/or disables the interaction of the driving part 52 with the actuating element 36 of the indicator device 25 in the locked state as schematically shown in the schematically enlargement of FIG. 12 which shows a similar part as FIG. 4. Preferably, the actuation through the insertion opening 54 is disabled in the locked state of the indicator device 25. In this shown state, the container 3 is in its tensioned position and the driving part 52. However already in the non-tensioned position of container 3, the bottom 34a of the signal element/blocking part is preferably very close to the bottom 53 of housing part 18/nebulizer 1, so that the relation between driving part 52 and indicator device is very similar in the non-shown non-tensioned state of the nebulizer. Preferably, in the locked state of the indicator device 25, the bottom 34a of the signal element 34 almost touches the bottom 53 of the nebulizer 1 (already in the non-tensioned state).

Preferably, the driving part 52 has been retracted from the actuator mechanism in the indicator device 25 in the locked state and in particular is not contacting/interacting with the actuating element 36 anymore. Preferably, the tip or actuation surface of the driving part 52 is not touching any part of the indicator device 25 in the locked state of the indicator device.

Preferably, the indicator element 35 causes the actuation of the actuation spring 47 and/or the transition of the signal element 34/blocking part from its first to second position, i.e. the locking of the indicator device 25, when the predetermined number of uses has been reached or exceeded.

In the present embodiment, the indicator element 35 comprises preferably a control portion 35d and/or a protrusion 35e which (upon the last rotary movement of the indicator element) releases the signal element 34 for detection of the locked state which results in locking the nebulizer 1 or current container 3 against further use.

Preferably, the control portion 35d comprises a protruding inclined surface which allows or initiates movement of the blocking part/signal element 34 into a blocking position. Preferably, the blocking part/signal element 34 disables the interaction of the driving part 52 with the indicator device in the blocking position, i.e. in the locked state. Preferably the control portion 35d is a protrusion or ridge on the lower side of the rotatable indicator element 35.

Preferably (as in the embodiments shown in the figures), the blocking part/signal element 34 is axially held in its first position (in the initial state of the indicator device 25) by a form-fit with the indicator housing 31. Preferably, the initial form-fit between the indicator housing 31 and the blocking part/signal element 34 is ended by a relative rotary movement between the blocking part/signal element 34 and the indicator housing 31. In particular, the signal element 34 comprises at least one, preferably multiple (for instance five or six) radially extending protrusions or holding portions 34d which rest in respective recesses or on respective shoulders of the indicator housing 31. Adjacent to the recesses or shoulders, the indicator housing 31 comprises longitudinally extending grooves 31d, preferably on the inside of an outer wall 310 of the indicator housing 31. Preferably, the protrusion or holding portion 34d engages on a shoulder between a part of a wall of the indicator housing 31 and the groove 31d in the initial state. Preferably the protrusion or holding portion 34d radially abuts a part of a wall of the indicator housing (on the holding portion's 34d far side of the groove 31d). Upon rotary movement of the signal element 34, the engagement of the at least one protrusion or holding portion 34d with the indicator housing (i.e. with the respective shoulder or recess) is ended and the protrusion or holding portion 34d can slide into the groove 31d (downwards in FIG. 10b and FIG. 10c), in particular driven by the force of the actuation spring 47.

Preferably, the indicator element 35 causes the rotary movement of the signal element 34, in particular by an engagement of at least one protrusion 35e (longitudinally extending on the indicator element's 35 side which faces the signal element 34) with the signal element 34 or its holding portion 34a. In particular, when the predetermined number of uses has been reached, the protrusion 35e abuts the side of holding portion 34d and the last rotary movement of the indicator element 35 pushes the holding portion 34d towards the groove 31d.

Initially, the signal element 34 is preferably secured against rotational movement, in particular by the indicator housing 31. In particular (as shown in FIG. 10b and FIG. 10c), the indicator housing 31 comprises a latching element or flexible arm 31f that abuts a holding portion 34d in rotary direction on the side of the respective groove 31d and thus prevents the signal element 34 from moving out of engagement with the indicator housing 31. Preferably, the latching element or flexible arm 31f is flexible in radial direction, in particular flexible radially inwards. Preferably the latching element or flexible arm 31f comprises an inclined surface or inclination 31g. Preferably this inclined surface or inclination 31g serves as a control surface for disengaging the rotational securement of the signal element 34 (relative to the indicator housing 31).

Preferably, the indicator element 35 comprises a control portion 35d, preferably with an inclination corresponding to the inclination 31g. When the predetermined number of uses has been reached or is about to be reached (for instance with the next rotary movement of the indicator element 35), the control portion 35d of the indicator element 35 has been moved into contact with the inclination 31g on the flexible arm 31f. Upon further rotation of the indicator element 35, the control portion 35d radially presses against inclination 31g and thus the flexible arm 31f is flexed away or radially inwards. When the flexible arm 31f is flexed radially inwards, the abutment between the flexible arm 31f and the holding portion 34d ends and/or the rotational securement of the signal element 34 is ended and the holding portion 34d can be pushed towards the respective groove 31d.

Preferably, the rotary securement of the blocking part/signal element 34 is ended only shortly before or simultaneously with actuating the signal element 34 (i.e. pushing the holding portions 34d out of axial engagement with the indicator housing 31g in the initial position). The figures show an embodiment of the indicator device 25 with a reduced and/or non-linear transmission. The incremental movement of an indicator element 35 being the last rotary part to be moved through a reduced transmission is comparatively small, for instance in the range of 2° to 7° (or 5° in a specific example). In order to ensure a reliable actuation of the signal element 34 and/or a quick succession of ending the rotational securement of the signal element 34 and rotating the signal element 34, the rotary movement of the indicator element 35 is sped up and/or the increment of rotary movement of the indicator element 35 is increased when the predetermined number of uses has been reached or is about to be reached. In particular (as shown in FIGS. 10a and 10b), the transmission 40 or gear ring 40b comprises a double cog 40e. This double cog 40e is formed by two gear ring cogs that are spaced so closely to each other that a gear cog 41b can mesh or fit between them and/or that both gear ring cogs forming the double cog 40e can engage with two gear cogs 41b simultaneously. Preferably this double cog 40a only engages with gear 41 when the predetermined number of uses has been reached or is about to be reached. When the double cog 40e engages with gear 41 the incremental movement of gear 41 along gear rim 31b and thus the incremental movement of indicator element 35 is increased (for instance, in a specific example the indicator element 35 is rotated about 10° around the rotational axis when the predetermined number of uses has been reached instead of a normal rotational path of 5°).

Preferably, the actuated blocking part/signal element 34 is secured in its second position and/or secured against axial displacement relative to the indicator housing 31. Preferably, the indicator device 25 remains in its locked state once the locked state has been entered. Preferably, the blocking part/signal element 34 is held by form-fit or snap-fit engagement in the second position i.e. in the locked state.

Preferably, a flexible element locks the signal element 34 in its second position and/or prevents that the signal element 34 can be pushed upwards or into the indicator housing 31 again. In particular, the indicator device 25 comprises at least one blocking spring 43 (preferably two blocking springs) that locks the indicator device in its locked state once the locked state has been entered. In the embodiment shown in FIG. 10c, the blocking spring 43 is preferably arranged between the advancing element 39 and the inner wall 31i of the indicator housing 31. Preferably the at least one blocking spring is biased radially outwards. Preferably, the at least one blocking spring 43 is made of metal, in particular spring steel. In particular, the at least one blocking spring 43 is a bent leaf spring forming two wings wherein preferably one wing abuts the advancing element 39 or an inner rim of the signal element 34 and the other wing rests against the inner wall 31i of the indicator housing.

When the signal element 34 is moved into its second position the advancing element 39 and the at least one blocking spring 43 are preferably axially moved together with the signal element 34. Preferably the width of the at least one blocking spring 43 is smaller than the distance by which the signal element is moved when it is transferred from its first position into its second position.

Preferably the blocking spring 43 radially expands or flexes outwards when the signal element 34 is moved into its second position, i.e. when the indicator device enters its locked state (when the signal element 34 is moved downwards with blocking spring 43 in FIG. 10c, the outer wing of blocking spring 43 does not abut against the inner wall 31i of the indicator housing 31 anymore, but can expand under the lower end of wall 31i). Preferably, in the locked state the blocking spring 43 extends at least partly transversal or diagonally to the inner wall 31i of the indicator housing 31 and/or extends in a plane outside or below the indicator housing 31. In this preferred embodiment, the reverse movement of the signal element 34 back into the indicator housing 31 is prevented by the barrier the at least blocking spring 43 forms in the path of the relative movement of the inner wall 31i. The at least one blocking spring 43 preferably holds the bottom 34a of the signal element 34 apart from the indicator housing 31.

Alternatively or additionally the holding portions 34d may form flexible hooks that engage in radial recesses in the bottom end of groove 31d in the indicator housing 31 (not shown embodiment).

In particular, the locked indicator device 25 or activated signal element 34 or associated blocking part results in particular in that the container 3 (with the attached indicator device) cannot move inside the closed housing of the nebulizer 1 in the stroke-like fashion as previously and as required for normal or further use so that normal use is prevented.

In particular, the locking of the indicator device 25 or disabling of the interaction with actuation element 36 results in that the nebulizer 1 or housing part 18 is at least partially opened when the nebulizer 1 is tensioned once more or when it is partially tensioned. FIG. 13 shows this state (partially tensioned nebulizer 1 with partially opened housing part 18) in a schematic, longitudinal section of the nebulizer 1. During the tensioning process the container 3 is moving downwardly together with the indicator device 25. Starting from the non-tensioned state (upper position of the container 3), the indicator device 25 abuts soon with its blocking part/signal element 34 or bottom 34*a* of the signal element 34 against the housing part 18 or bottom 53 of the nebulizer 1, so that a further usual downward movement is not possible.

Preferably, in the locked state the bottom 34*a* of the signal element 34 is significantly closer to the bottom 53 of the nebulizer 1/of the lower housing part 18 than in the unlocked state. Preferably, in the locked state of the indicator device 25, the distance between the bottom 53 of the nebulizer 1 and bottom 34a of the signal element 34 is (significantly) smaller than the distance the container 3 travels in a full tensioning process.

In particular, the blocking part/signal element 34 restricts the axial moveability of the container 3 in the nebulizer 1 in the locked state. Due to the force applied when tensioning the nebulizer 1 and due to the resulting axial force in the movement of the container 3, the housing part 18 will be moved outwards or relative to the nebulizer 1, inner part 17 or upper part 16 together with the container 3 and indicator device 25 during the further tensioning movement in axial direction in the locked state.

Preferably, when the indicator device 25 abuts against the housing part 18 or the bottom 53 of the nebulizer 1 during the tensioning process with a locked indicafor device 25, the complete bottom of the blocking part/the complete bottom 34a of the signal element 34 abuts or contacts against the housing part 18 or bottom 53 of the nebulizer 1. Thus the area which transfers the tensioning forces and/or downward movement from the container movement via the indicator device 25 to the housing part 18 is maximized (i.e. the risk of these forces damaging the housing part 18 and thus its reusability is minimized).

The above common downward movement of container 3, indicator device 25 and housing part 18 is possible due to a respectively constructed fastening of the housing part 18 at the nebulizer 1. In particular, the retaining force is selected or set such that it can be overcome by the downward movement of the container 3.

In the present embodiment, the retaining element 19 engages with a retaining nose 64 in a respective retaining recess 65 in the housing part 18 or vice versa. Thus, substantially an undercut or indention can be realized. However, the abutting shoulders which extend at least essentially radially of the nose 64 on one hand and the recess 65 on the other hand are slightly inclined, preferably by about 1° to 5° to the radial plane such that the axial force of the tensioning process can overcome the retaining force provided by the engagement of the nose 64 into the recess 65 so that the retaining element 19 is flexed radially and the retaining engagement is overcome. Consequently, the housing part 18 is moved downwardly as well and, thus, is pushed at least partly from the nebulizer 1 or separated from the upper housing part 16 and/or pushed from the inner part 17.

Preferably, the bottom 34a of the signal element 34 and the bottom 53 of the nebulizer 1/housing part 18 are so closely spaced in the locked state of the indicator device 25, that the above mentioned opening of the fastening between housing part 18 and retaining element 19 by the axial force of the tensioning process already occurs in the first half of the total rotation angle necessary for tensioning the nebulizer 1 by turning the lower housing part 18 relative to the upper housing part 16. Thus early in the tensioning process, a (partly) opening of the housing also indicates the locked state of the indicator device 25.

This pushing or axial displacement of the housing part 18 or any other opening of the nebulizer 1 results preferably in that the nebulizer 1 is locked against further use by means of the locking device 26. Therefore, the indicator device 25 or its blocking part/signal element 34 effects indirectly via the opening of the nebulizer 1 the desired locking of the nebulizer 1 in the locked state.

In the preferred embodiment, the locking device 26 blocks tensioning of the nebulizer 1 in the locked state.

Preferably, the locking device 26 comprises a moveable locking element 66 and an associated locking spring 67. The locking element 66 is preferably axially moveable between a locked position and an unlocked position. The locking element 66 is preferably biased into the locked position by the locking spring 67.

In the locked position, the locking element 66 is preferably in its lower axial position shown in FIG. 13. FIG. 14 shows an enlargement of the smaller encircled area of FIG. 13.

In the locked position, the locking element 66 blocks rotation of the inner part 17 relative to the outer part 16 and, thus, blocks (further) tensioning of the nebulizer 1. This is preferably achieved in the present embodiment in that the locking element 66 moves or engages preferably axially into a respective pocket 68 formed in the upper part 16 such that said relative rotation is blocked. In particular, the locking element 66 engages with an engagement portion 69 into the respective recess or pocket 68 such that any further rotation and/or back rotation is prevented. However, other constructional solutions are possible as well.

The locking device 26, in particular the locking element 66 and the locking spring 67, are preferably arranged and/or supported by the inner part 17 and/or extend between the inner part 17 and upper part 16.

The nebulizer 1, inner part 17 or locking device 26 comprises preferably a cover 70 covering the locking device 26 at least on the periphery of the lower part 17b of the inner part 17 in order to prevent or at least complicate any undesired manipulation of the locking device 26 or locking element 66 by a user or patient.

Preferably, the locking device 26 or locking element 66 is locking relative rotation or further rotation before the complete tensioned state or position is reached, i.e. preferably in an intermediate position, most preferably in the second half of the total rotation angle necessary for tensioning the nebulizer 1 by turning the lower housing part 18 relative to the upper housing part 16.

This intermediate blocking has the advantage that it is preferably not possible to fully actuate the nebulizer 1 as it is not possible to reach complete tensioning and, thus, the nebulizer's gear or transmission transforming the relative rotation into the axial stroke of the holder 6 actually holds the holder 6 in the intermediate position and does not allow any axial back movement into the upper, non-tensioned position. With the intermediate blocking in place, the nebulizer is in its fully locked state.

Alternatively or additionally, it is also possible that the locking device 26 or its locking element 66 locks the release of the spring 7 or holder 6 to dispense the fluid 2, in particular by locking any depression of blocking element 8 (or any actuation the of button 8b) and, thus, blocking the release. However, other constructional solutions are possible as well.

FIG. 5c and FIG. 14 show details of the locking device 26 of the nebulizer 1 in similar schematic sections, however with the locking device 26 in the unlocked position in FIG. 5c, i.e. the locking element 66 in the upper position and with the locking device 26 in the locked position in FIG. 14, i.e. the locking element 66 in the lower position. The locking device 26 or locking element 66 is brought into the upper position or is unlocked preferably only by closing the nebulizer 1, in particular by the housing part 18 in the completely attached or closed position.

In the shown embodiment, the housing part 18 comprises a preferably finger-like and/or axially extending actuator 71 which extends into the locking device 26 and/or into the cover 70 and/or axially abuts and/or pushes the locking element 66 into its unlocking position (upper position), as shown in FIG. 5a (in comparison with locked state in FIG. 13). Thus, only the completely closed nebulizer 1 or housing part 18 unlocks the locking device 26 and, thus, unlocks the nebulizer 1.

The actuator 71 is preferably arranged within the housing part 18 so that any manipulation is not possible or at least complicated.

When the nebulizer 1 is in the locked state and, preferably when the nebulizer 1 or its housing part 18 has been opened partially by the last tensioning process, any further use of the nebulizer 1 with the container 3 and the indicator device 25 in its locked state is not possible. The locking device 26 locks preferably automatically. Preferably, the locking spring 67 biases the locking element 66 into the locking position, so that upon at least partial opening of the nebulizer 1 or (axial) displacement of its housing part 18, the locking device 26 or its locking element 66 can move and moves into the locking position.

Preferably, the locking element 66 is moveable (essentially or only) in axial direction.

After replacement of the current container 3 with its locked indicator device 25 (blocking part/signal element 34 in the blocking position) against a new container 3 including a new or reset indicator device 25, the nebulizer 1 or its housing part 18 can be closed completely again. Thus, the nebulizer 1 or its locking device 26 can be or is unlocked again. Preferably, the actuator 71 pushes the locking element 66 back into its unlocking position.

Thus, the locking device 26 is reset or unlocked again, preferably by (completely) closing the nebulizer 1, its housing 24 or housing part 18, and the nebulizer 1 can be used with the new container 3 as previously.

Preferably, the container 3 is or has to be replaced in an at least partially tensioned state of the nebulizer 1, in particular such a tensioned state that complete closing of the nebulizer 1 or its housing 24 is not possible when the indicator device 25 is in the locked state or when the insertion opening 54 is closed.

In particular, the locking element 66 may form or may be formed by a sliding block.

In the present embodiment, the locking spring 67 is preferably arranged at the lower part 17b of the inner part 17 and/or at the lower end of the locking device 26 or locking element 66, or near or adjacent to the housing part 18. However, the locking spring 67 can also be arranged at the other end and/or within the upper housing part 16 of the nebulizer 1 and/or at any other convenient location.

In the present embodiment, the locking spring 67 is preferably a push-spring. However, a pull-spring could be used alternatively.

In the present embodiment, the locking spring 66 is preferably a helical spring. However, it could be used alternatively e.g. a flat spring or leaf spring or any other spring.

In the present embodiment, the locking element 66 and the locking spring 67 are formed by separate parts. However, it is generally also possible to integrate the locking element 66 into the locking spring 67 or vice versa.

It has to be noted that the piercing part 48 is preferably received within the indicator device 25 or its housing 31, but can protrude outwards in the actuated state.

It has to be noted that alternatively, the disabling of the interaction of the driving part 52 and the indicator device 25 can be omitted. Instead, the indicator device 25 or blocking part/signal element 34 can more or less directly communicate with or actuate the locking device 26 or, for example, the retaining element 19 or blocking element 8 in order to cause a direct or indirect locking of the nebulizer 1 or container 3 against further use.

Instead of the preferably linear or sled-like moveable blocking part/signal element 34, any other motion, in particular a radial and/or pivotal movement, is possible, in particular for partially or completely restricting the moveability of the container 3 (with the attached indicator devise 25) in the closed housing 24 of the nebulizer.

Alternatively, the signal element 34 or blocking part can move outwards from the indicator device 25 or its housing 31, preferably transversally and/or at one side of the indicator housing 31 for locking at least one engagement possibility and/or actuating any other component in the locked state or for locking the nebulizer 1 and/or container 3.

Alternatively or additionally, the signal element 34 or blocking part can engage into or abut against a section or contour of the housing part 18 and/or nebulizer housing 24 or the like in order to restrict or prevent operation or movement in the locked state in order to block further use of the nebulizer 1 and/or container 3 in the locked state.

The signal element or blocking part, in particular also when acting radially, are preferably biased by spring 47 or any other spring means. The spring or spring means can be formed integrally and/or by plastic parts or pieces. Alternatively, a spiral or clock spring or any other spring, such as helical spring 47 or the like, could be used for biasing the signal element 34 or blocking part, preferably into the locked state.

It is also possible that the driving part 52 directly drives or actuates the gear 41. In this case, the driving part 52 is preferably elastically supported by the housing part 18, in particular via a spring means (not shown), in particular for compensating axial tolerances and/or allowing radial or transversal flexing of the driving part 52. Additionally or alternatively, the driving part 52 may be flexible in order to allow transversal flexing for engaging with the gear 41 only in one direction of relative axial movement to the gear 41 to rotate the gear 41 only in one rotational direction.

The indicator device 25 can comprise any other counting mechanism, in particular as described in WO 2009/037085 A1, page 4, line 19 to page 10, line 13, which is incorporated herein by reference. Such a counting mechanism can also trigger, release or actuate the signal element 34 or blocking part. When using this counting mechanism, the rotatable indicator element 35 can also release or control the release of the signal element 34 or blocking part in the locked state to move into the locking position.

In particular, the driving part 52 may engage the hub of the counting mechanism shown in WO 2009/037085 A1 or the like and/or drive or actuate the indicator device 25 or counting. The signal element 34 or blocking part is independent from the counting, the functions are separated.

The container 3 or indicator device 25 or insertion opening 54 may be provided with an optional protection (not shown), which covers in particular the insertion opening 54 before the first use.

Preferably, the protection has to be removed before the container 3 and/or indicator device 25 can be inserted into the nebulizer 1 or housing part 18.

Preferably, the protection extends transversally over the indicator device 25 or its housing 31 and/or over the container 3 and/or has a larger diameter than the indicator device 25 and/or container 3, in particular such that it does not fit into the nebulizer 1 or housing part 18.

Preferably, the protection can be removed only irreversibly, i.e. cannot be reconnected after removal.

Preferably, the protection covers or closes the insertion opening 54 and/or the indicator device 25.

Preferably, the protection is connected to the indicator device 25 or container 3 by form-fit or force-fit and/or by a snap-fit or click-fit.

As already mentioned, individual features, aspects and/or principles of the embodiments described may also be combined with one another as desired and may be used particularly in the shown nebulizers 1 but also in similar or different nebulizers.

Features of the different embodiments can be combined or exchanged.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g. powder inhalers or so-called metered dose inhalers.

Preferably, the fluid 2 is a liquid, as already mentioned, especially an aqueous pharmaceutical formulation or an ethanolic pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed in particular in WO 2009/115200 A1, preferably on pages 25 to 40, or in EP 2 614 848 A1, paragraphs 0040 to 0087, which are incorporated herewith by reference. In particular, these may be aqueous or non-aqueous solutions, mixtures, formulations containing ethanol or free from any solvent, or the like.

LIST OF REFERENCE NUMERALS 1 nebulizer
2 fluid
3 container
4 bag
5 pressure generator
6 holder
7 drive spring
8 blocking element
8b button
9 conveying tube
10 non-return valve
11 pressure chamber
12 nozzle
13 mouthpiece
14 aerosol
15 air supply opening
16 upper housing part
17 inner part
17a upper part of inner part
17b lower part of inner part
18 housing part (lower part)
19 retaining element
20 aeration spring
21 container base
22 piercing element
23 venting hole
24 nebulizer housing
25 indicator device
26 locking device
27 mouthpiece cover
28 head
29 container housing
30 container edge
31 indicator housing
31a window
31b gear rim
31c recesses
31d (longitudinal) groove
31f flexible arm
31g inclination
31i inner wall
31o outer wall
32 gripping section
33 upper part
34 signal element
34a bottom (of signal element)
34b groove
34c clip
34d holding portion
34w (cylindrical) wall
35 indicator element
35a bearing
35b marking
35c latching arm (on indicator element)
35d control portion
35e protrusion
36 actuation element
36a guide element
36b support structure
36c actuation surface
37 ratchet element
37a latching arm
37b saw teeth (on ratchet element)
38 biasing spring
39 advancing element
39a guide track
39b tooth39c flexible arm
40 transmission
40a first set of saw teeth
40b gear ring
40c second set of saw teeth
40d tubular section (on transmission)
40e double cog
41 gear
41a axle section
41b cog (on gear)
43 blocking spring
47 actuation spring
48 piercing part
49 piercing tip
50 foil
51 indention
52 driving part
53 bottom
54 insertion opening
64 retaining nose
65 retaining recess
66 locking element 67 locking spring
68 pocket
69 engagement portion
70 cover
71 actuator
72 sliding guide
73 base portion

The invention claimed is:

1. A nebulizer (1) for a fluid (2), the nebulizer (1) comprising:
a nebulizer housing (24) having a housing part (18);
a replaceable container (3) containing the fluid (2) and being disposed in an inner volume defined by the nebulizer housing (24), wherein the nebulizer housing (24) is opened for replacing the replaceable container (3) by detaching the housing part (18) from the nebulizer (1); and
an indicator device (25) for counting or indicating a number of uses performed or still possible with the replaceable container (3), wherein the indicator device (25) is disposed within an indicator housing (31), which is both inseparably connected with the replaceable container (3) and separable from the nebulizer housing (24) and the housing part (18), such that the indicator device (25) is replaced with the replaceable container (3) to which it is inseparably connected;
wherein the indicator device (25) comprises a blocking part for preventing further use of the replaceable container (3) in a locked state of the indicator device (25) when a predetermined number of uses has been reached or exceeded with the replaceable container (3), and
wherein the blocking part is at least one of: integrated into the indicator housing (31), forms part of the indicator housing (31), and is arranged inside the indicator housing (31).

2. The nebulizer (1) according to claim 1, wherein the blocking part can be moved parallel to a longitudinal or dispensing direction of the replaceable container (3) or nebulizer (1).

3. The nebulizer (1) according to claim 1, wherein in that in the locked state, the blocking part blocks complete axial or stroke-like movement of the replaceable container (3) in the nebulizer housing (24) when the nebulizer housing (24) is closed and when the predetermined number of uses has been reached or exceeded with the replaceable container (3).

4. The nebulizer (1) according to claim 1, wherein in the locked state, the indicator device (25) or the blocking part causes at least partial opening of the nebulizer housing (24) or at least partial detachment of the housing part (18) when the predetermined number of uses has been reached or exceeded with the replaceable container (3).

5. The nebulizer according to claim 4, wherein the nebulizer (1) is adapted to block further use or tensioning when the nebulizer housing (24) is at least partially open or the housing part (18) is at least partially detached.

6. The nebulizer according to claim 1, wherein the indicator device (25) comprises an indicator element (35) which actuates the blocking part so that it is moved from an initial position in the indicator housing (31) to a locking position.

7. The nebulizer according to claim 6, wherein the indicator device (25) comprises a blocking spring (43) preventing a back movement of the blocking part from the locking position to the initial position.

8. The nebulizer according to claim 1, wherein the indicator device (25) comprises a signal element (34) or flag which, when the locked state of the indicator device (25) is entered, when the predetermined number of uses of the nebulizer (1) with the replaceable container (3) has been reached or exceeded, or when the replaceable container (3) is empty, becomes visible or more visible or indicates the locked state of the indicator device (25).

9. The nebulizer according to claim 8, wherein the indicator device (25) comprises an indicator element (35), which actuates the signal element (34) or flag so that the signal element (34) or flag becomes visible or more visible to indicate when the locked state of the indicator device (25) is entered, when the predetermined number of uses of the nebulizer (1) with the replaceable container (3) has been reached or exceeded, or when the replaceable container (3) is empty.

10. The nebulizer according to claim 8, wherein when actuated, the signal element (34) or flag is moved from a first position in the indicator housing (31) of the indicator device (25) to a second position in which the signal element (34) or flag at least partly extends from the indicator housing (31).

11. The nebulizer according to claim 8, wherein the blocking part forms or is formed by the signal element (34).

12. The nebulizer according to claim 1, wherein the nebulizer (1) comprises a driving part (52) for actuation of the indicator device (25) and the blocking part disables the counting or the actuation of a counting mechanism in the indicator device (25) or disables an interaction of the driving part (52) with the indicator device (25) in the locked state.

13. The nebulizer according to claim 1, wherein the indicator device (25) comprises an insertion opening (54) which allows insertion of a driving part (52) of the nebulizer (1), or interaction of the driving part (52) with an actuator element (36) of the indicator device (25) in an unblocked state of the indicator device (25).

14. The nebulizer according to claim 1, wherein the nebulizer (1) comprises a driving part (52) for driving, actuating, or triggering the indicator device (25), or for opening or piercing the replaceable container (3).

15. The nebulizer according to claim 1, wherein the indicator device (25) is fixedly arranged at a base (21) of the replaceable container (3), fixedly arranged opposite to an outlet or head (28) of the replaceable container (3), or connected by snap-fit or form-fit with the replaceable container (3).

16. The nebulizer according to claim 1, wherein the indicator device (25) comprises a piercing part (48) for opening an aeration of the replaceable container (3).

17. The nebulizer according to claim 16, wherein the piercing part (48) is axially moveable or is located or biased inside the indicator housing (31) of the indicator device (25), when not actuated.

18. A container (3) for replaceable use in a nebulizer (1), the container (3) containing a fluid (2), and the container (3) comprising:
an outlet and a base (21) opposite to the outlet;
an indicator device (25) for counting and/or indicating a number of uses performed or still possible with the container (3) before replacement,
wherein the indicator device (25) is disposed within an indicator housing (31) that is fixedly and inseparably connected to the base (21) of the container (3),
wherein the indicator device (25) comprises a blocking part for preventing further use of the container (3) in a locked state of the indicator device (25) when the predetermined number of uses has been reached or exceeded, wherein the blocking part is at least one of: integrated into the indicator housing (31), forms part of the indicator housing (31), and is arranged inside the indicator housing (31), wherein the indicator device (25) comprises an indicator element (35), which actuates the blocking part so that it is moved from an initial position in the indicator housing (31) to a locking position when the predetermined number of uses has been reached or exceeded with the container (3), and wherein the indicator device (25) comprises a blocking spring (43) preventing a back movement of the blocking part from the locking position to the initial position.

19. The container according to claim 18, wherein the blocking part can be moved parallel to a longitudinal or dispensing direction of the container (3).

20. The container according to claim 18, the blocking part forms or is formed by a signal element (34), which, when the locked state of the indicator device (25) is entered, when the predetermined number o uses of the container (3) has been reached or exceeded, or when the container (3) is empty, is moved from a first position in the indicator housing (31) of the indicator device (25) to a second position in which the signal element (34) partly extends from the indicator housing (31), or in which the signal element (34) is visible or more visible than in the first position.

21. The container according to claim 18, wherein the indicator device (25) comprises a piercing part (48) for opening an aeration of the container (3).

22. The container according to claim 18, wherein the indicator device (25) is connected by snap-fit or form-fit to the container (3).

23. The container according to claim 18, wherein the blocking part disables a counting mechanism in the indicator device (25) or prevents the interaction of the nebulizer (1) with an actuator element (36) of the indicator device (25) in the locked state of the indicator device (25).

24. A container (3) for replaceable use in a nebulizer (1), the container (3) containing a fluid (2), and the container (3) comprising:

an outlet and a base (21) opposite to the outlet;

an indicator device (25) for counting and/or indicating a number of uses performed or still possible with the container (3) before replacement, wherein the indicator device (25) is directly, annularly and fixedly attached to the base (21) of the container (3), wherein the indicator device (25) comprises a signal element (34) or flag in which: (i) when a predetermined number of uses of the container (3) has been reached or exceeded or when the container (3) is empty, the signal element (34) or flag becomes visible or more visible, and (ii) when the predetermined number of uses of the container (3) has not been reached, the signal element (34) or flag is not visible or less visible as compared with when the predetermined number of uses of the container (3) has been reached or exceeded, and wherein the indicator device (25) comprises an indicator housing (31), and, when actuated, the signal element (34) or flag is moved from a first position in the indicator housing (31) of the indicator device (25) to a second position in which the signal element (34) or flag at least partly extends from the indicator housing (31).

25. The container according to claim 24, wherein the indicator device (25) comprises an indicator element (35) which actuates the signal element (34) or flag so that the signal element (34) or flag becomes visible or more visible or indicates when the predetermined number of uses of the container (3) has been reached or exceeded or when the container (3) is empty.

26. The container according to claim 24, wherein the indicator device (25) comprises a blocking spring (43) preventing a back movement of the signal element (34) or flag from the second position to the first position.

27. A nebulizer (1) for a fluid (2), the nebulizer (1) comprising:

a nebulizer housing (24) having a central axis;

a replaceable container (3) containing the fluid (2) and being disposed in an inner volume defined by the nebulizer housing (24), wherein the replaceable container (3) is axially movable relative to the nebulizer housing (24) during conveying of the fluid (2) to be nebulized and during nebulization of the fluid (2); and an indicator device (25) for counting and/or indicating a number of uses performed or still possible with the replaceable container (3); and a driving part (52) for actuating the indicator device (25) upon movement of the replaceable container (3) relative to the driving part (52), wherein the driving part (52) is stationary, non-movable, and co-axially located relative to the nebulizer housing (24).

28. The nebulizer according to claim 27, wherein the nebulizer housing (24) comprises a detachable housing part (18) such that the nebulizer housing (24) is opened for replacing the replaceable container by detaching the housing part (18) from the nebulizer, wherein the driving part (52) is a part of the housing part (18).

29. The nebulizer according to claim 27, wherein the driving part (52) affects the opening of the replaceable container (3) by movement of the replaceable container (3) relative to the driving part (25).

* * * * *